(12) United States Patent
Hou

(10) Patent No.: US 12,385,906 B2
(45) Date of Patent: Aug. 12, 2025

(54) METHODS OF DETECTION OF COMPOUND, ANTIBODY OR PROTEIN USING RECOMBINANT ENDOSPORES OR BACTERIA AS SENSING ELEMENT

(71) Applicant: NATIONAL TAIPEI UNIVERSITY OF TECHNOLOGY, Taipei (TW)

(72) Inventor: Shao-Yi Hou, Taipei (TW)

(73) Assignee: NATIONAL TAIPEI UNIVERSITY OF TECHNOLOGY, Taipei (TW)

( * ) Notice: Subject to any disclaimer, the term of this patent is extended or adjusted under 35 U.S.C. 154(b) by 532 days.

(21) Appl. No.: 17/670,818

(22) Filed: Feb. 14, 2022

(65) Prior Publication Data
US 2022/0236260 A1  Jul. 28, 2022

Related U.S. Application Data

(63) Continuation of application No. 16/813,028, filed on Mar. 9, 2020, now Pat. No. 11,275,082.

(51) Int. Cl.
*G01N 33/543* (2006.01)
*C12Q 1/02* (2006.01)

(52) U.S. Cl.
CPC ......... *G01N 33/54306* (2013.01); *C12Q 1/02* (2013.01)

(58) Field of Classification Search
CPC .............................................. G01N 33/54306
See application file for complete search history.

(56) References Cited

U.S. PATENT DOCUMENTS

| 5,420,016 | A | 5/1995 | Boguslaski et al. |
| 11,275,082 | B2 * | 3/2022 | Hou .......................... C12Q 1/02 |

OTHER PUBLICATIONS

Nguyen et al., "Killed *Bacillus subtilis* spores expressing streptavidin: a novel carrier of drugs to target cancer cells," Journal of Drug Targeting, vol. 21, No. 6, 2013, pp. 528-541.
Heinisch, et al., "*E. coli* surface display of streptavidin for directed evolution of an allylic deallylase," Chemical Science, 2018, vol. 9, No. 24, pp. 5383-5388.
Unknown Author, "Hapten Detection Using Nanogold and Lateral Flow Strip," Chemical Engineering & Biotechnology Department, National Taipei University of Technology (with translation).
Kim, J., Schumann, W., "Display of proteins on Bacillus subtilis endospores" Cell Mol. Life Sci., 2009; 66: 3127-3136.
Van Bloois, E., et al., "Decorating microbes: surface display of proteins on *Escherichia coli*" Trends Biotechnol. 2011; 29(2): 79-86.
Francisco, et al. "Transport and anchoring of ß-lactamase to the external surface of *Escherichia coli*" Proc. Natl. Acad. Sci. USA, 1992; 89: 2713-2717.
Georgiou, et al.. "Display of β-lactamase on the *Escherichia coli* surface: outer membrane phenotypes conferred by Lpp'-OmpA'-β-lactamase fusions" Protein Engineering, 1996; 9(2): 239-247.
Nguyen, et al. "Use of IPTG-inducible promoters for anchoring recombinant proteins on the *Bacillus subtilis* spore surface" Protein Expression and Purification, 2014; 95: 67-76.
Al-Hinai, M. A., et al. "The Clostridium Sporulation Programs: Diversity and Preservation of Endospore Differentiation" Microbiology and Molecular Biology Reviews, 2015; 79(1): 19-37.
Setlow, P. "Germination of Spores of *Bacillus* Species: What We Know and Do Not Know" Journal of Bacteriology, 2014; 196(7): 1297-1305.
Henriques, A.O., et al. "Functional architecture and assembly of the spore coat" in Ricca E, Henriques AO, Cutting SM (eds): Bacterial Spore Formers: Probiotics and Emerging Applications. London, Horizon Science Press, 2004, pp. 34-52.
McKenney, P.T., et al. "The *Bacillus subtilis* endospore: assembly and functions of the multilayered coat" Nature Reviews Microbiology, 2013; 11: 33-44.
Takamatsu, H., et al. Assembly and genetics of spore protective structures Cell Mol. Life Sci., 2002; 59: 434-444.
Isticato, R., et al. "Surface Display of Recombinant Proteins on *Bacillus subtilis* Spores" J. Bacteriol., 2001; 183(21): 6294-6301.
Isticato, R., et al. "Spore Surface Display" Microbiol. Spectr., 2014; 2(5), 15 pages.
Lequin, R. M. "Enzyme Immunoassay (EIA)/Enzyme-Linked Immunosorbent Assay (ELISA)" Clinical Chemistry, 2005; 51(12): 2415-8.
Schmidt, S.D., et al. "Aβ measurement by enzyme-linked immunosorbent assay" Methods in Molecular Biology, 2012; 849: 507-27.
Chittamma, A., et al. "Detection of In Utero Marijuana Exposure by GC-MS, Ultra-Sensitive ELISA and LC-TOF-MS Using Umbilical Cord Tissue" Journal of Analytical Toxicology, 2013; 37: 391-394.
Rowley, T. "Flow Cytometry—A Survey and the Basics" Mater Methods, 2012; 2:125.
Bereza-Malcolm, L.T., et al. "Environmental sensing of heavy metals through whole cell microbial biosensors: a synthetic biology approach" ACS Synth Biol., 2015; 4: 535-46.
Mehta, J., et al. "Progress in the biosensing techniques for trace-level heavy metals" Biotechnol. Adv., 2016; 34: 47-60.
Liu, Q., et al. "Cell-Based Biosensors and Their Application in Biomedicine" Chemical Reviews, 2014; 114: 6423-6461.
Tian, Y., Lu, Y., Xu, X., Wang, C., Zhou, T., Li, X. "Construction and comparison of yeast whole-cell biosensors regulated by two RAD54 promoters capable of detecting genotoxic compounds" Toxicol. Mech. Methods, 2017; 27: 115-120.

(Continued)

*Primary Examiner* — Brian Gangle
*Assistant Examiner* — Lakia J Jackson-Tongue
(74) *Attorney, Agent, or Firm* — Sughrue Mion, PLLC

(57) ABSTRACT

The present invention provides a method and a system for detecting the presence of an analyte in a sample. In particular, the present invention provides a system, such as a diagnostic kit, for detecting the presence of an analyte in a sample, comprising (a) a recombinant bacterium or spore expressing one or more recombinant proteins on the surface thereof, wherein the recombinant protein specifically binds to the analyte directly or through a binding agent that specifically binds to the recombinant protein and the analyte, and (b) a signal-producing substance that can be detected.

17 Claims, 16 Drawing Sheets
Specification includes a Sequence Listing.

(56) References Cited

OTHER PUBLICATIONS

Xu, T., et al. "A rapid and reagent-free bioassay for the detection of dioxin-like compounds and other aryl hydrocarbon receptor (AhR) agonists using autobioluminescent yeast" Analytical and Bioanalytical Chemistry, 2018; 410: 1247-1256.
Dusserre, C., et al. "Using bisphenol A and its analogs to address the feasibility and usefulness of the CALUX-PPARγ assay to identify chemicals with obesogenic potential" Toxicology in Vitro, 2018; 53: 208-221.
Smith, G. P., "Filamentous fusion phage: Novel expression vectors that display cloned antigens on the virion surface" Science 1985; 228(4705): 1315-1317.
Sany et al. "An overview of detection techniques for monitoring dioxin-like compounds: latest technique trends and their applications" RSC Adv., 2016; 6: 55415-55429.
Pan et al. 2014 FEMS Microbiology Letters, vol. 358, Issue 2, pp. 209-217 (Year: 2014).
Darwish 2006 Int J Biomed Sci. Sep; 2(3): 217-235 (Year: 2006).
Peruski et al. 2003 Clin Diagn Lab Immunol. Jul. 10(4): 506-513 (Year: 2003).
Kim, J.-H., et al. (2005) Biochemical and Biophysical Research Communications, 331:210-214.

\* cited by examiner

SEQUENCE LISTING

```
<160> NUMBER OF SEQ ID NOS: 7

<210> SEQ ID NO 1
<211> LENGTH: 380
<212> TYPE: PRT
<213> ORGANISM: Bacillus subtilis

<400> SEQUENCE: 1

Met Ser Lys Arg Arg Met Lys Tyr His Ser Asn Asn Glu Ile Ser Tyr
1               5                   10                  15

Tyr Asn Phe Leu His Ser Met Lys Asp Lys Ile Val Thr Val Tyr Arg
            20                  25                  30

Gly Gly Pro Glu Ser Lys Lys Gly Lys Leu Thr Ala Val Lys Ser Asp
        35                  40                  45

Tyr Ile Ala Leu Gln Ala Glu Lys Lys Ile Ile Tyr Tyr Gln Leu Glu
    50                  55                  60

His Val Lys Ser Ile Thr Glu Asp Thr Asn Asn Ser Thr Thr Thr Ile
65                  70                  75                  80

Glu Thr Glu Glu Met Leu Asp Ala Asp Phe His Ser Leu Ile Gly
                85                  90                  95

His Leu Ile Asn Gln Ser Val Gln Phe Asn Gln Gly Gly Pro Glu Ser
            100                 105                 110

Lys Lys Gly Arg Leu Val Trp Leu Gly Asp Asp Tyr Ala Ala Leu Asn
        115                 120                 125

Thr Asn Glu Asp Gly Val Val Tyr Phe Asn Ile His His Ile Lys Ser
    130                 135                 140

Ile Ser Lys His Glu Pro Asp Leu Lys Ile Glu Glu Gln Thr Pro Val
145                 150                 155                 160
```

```
Gly Val Leu Glu Ala Asp Asp Leu Ser Glu Val Phe Lys Ser Leu Thr
            165                 170                 175
His Lys Trp Val Ser Ile Asn Arg Gly Gly Pro Glu Ala Ile Glu Gly
        180                 185                 190
Ile Leu Val Asp Asn Ala Asp Gly His Tyr Thr Ile Val Lys Asn Gln
            195                 200                 205
Glu Val Leu Arg Ile Tyr Pro Phe His Ile Lys Ser Ile Ser Leu Gly
    210                 215                 220
Pro Lys Gly Ser Tyr Lys Lys Glu Asp Gln Lys Asn Glu Gln Asn Gln
225                 230                 235                 240
Glu Asp Asn Asn Asp Lys Asp Ser Asn Ser Phe Ile Ser Ser Lys Ser
                245                 250                 255
Tyr Ser Ser Ser Lys Ser Ser Lys Arg Ser Leu Lys Ser Ser Asp Asp
            260                 265                 270
Gln Ser Ser Lys Ser Gly Arg Ser Ser Arg Ser Lys Ser Ser Ser Lys
        275                 280                 285
Ser Ser Lys Arg Ser Leu Lys Ser Ser Asp Tyr Gln Ser Ser Lys Ser
    290                 295                 300
Gly Arg Ser Ser Arg Ser Lys Ser Ser Ser Lys Ser Ser Lys Arg Ser
305                 310                 315                 320
Leu Lys Ser Ser Asp Tyr Gln Ser Ser Lys Ser Ser Lys Arg Ser Pro
                325                 330                 335
Arg Ser Ser Asp Tyr Gln Ser Ser Arg Ser Pro Gly Tyr Ser Ser Ser
            340                 345                 350
Ile Lys Ser Ser Gly Lys Gln Lys Glu Asp Tyr Ser Tyr Glu Thr Ile
        355                 360                 365
Val Arg Thr Ile Asp Tyr His Trp Lys Arg Lys Phe
    370                 375                 380

<210> SEQ ID NO 2
<211> LENGTH: 1226
<212> TYPE: DNA
<213> ORGANISM: Artificial Sequence
<220> FEATURE:
<223> OTHER INFORMATION: Synthetic polynucleotide

<400> SEQUENCE: 2
ctgcagaaat cgtttgggcc gatgaaaaat cggctcttta ttttgatttg tttttgtgtc    60
atctgtcttt ttctatcatt tggacagccc ttttttcctt ctatgatttt aactgtccaa   120
gccgcaaaat ctactcgccg tataataaag cgtagtaaaa ataaggagg agtatatatg    180 ggttattaca aaaatacaa agaagagtat tatacggtca aaaaaacgta ttataagaag    240
tattacgaat atgataaaaa agattatgac tgtgattacg acaaaaaata tgatgactat    300
gataaaaaat attatgatca cgataaaaaa gactatgatt atgttgtaga gtataaaaag    360
cataaaaaac actacgcagc tgcacttgca cttgcagcac tactagcact agctctagct    420
atggtgagca agggcgagga gctgttcacc ggggtggtgc ccatcctggt cgagctggac    480
ggcgacgtaa acggccacaa gttcagcgtg tccggcgagg gcgagggcga tgccacctac    540
ggcaagctga ccctgaagtt catctgcacc accggcaagc tgcccgtgcc ctggcccacc    600
ctcgtgacca cctgaccta cggcgtgcag tgcttcagcc gctaccccga ccacatgaag    660
cagcacgact tcttcaagtc cgccatgccc gaaggctacg tccaggagcg caccatcttc    720
ttcaaggacg acggcaacta caagacccgc gccgaggtga agttcgaggg cgacaccctg    780
gtgaaccgca tcgagctgaa gggcatcgac ttcaaggagg acggcaacat cctggggcac    840
```

```
aagctggagt acaactacaa cagccacaac gtctatatca tggccgacaa gcagaagaac    900
ggcatcaagg tgaacttcaa gatccgccac aacatcgagg acggcagcgt gcagctcgcc    960
gaccactacc agcagaacac ccccatcggc gacggccccg tgctgctgcc cgacaaccac   1020
tacctgagca cccagtccgc cctgagcaaa gaccccaacg agaagcgcga tcacatggtc   1080
ctgctggagt tcgtgaccgc cgccgggatc actctcggca tggacgagct gtacaagtaa   1140
gcggcctaaa cgccattaac atctcctcgt ttttactttc ccccggctat tgccgggtct   1200
tttttgtttg tgcactatat ctcgag                                        1226
```

<210> SEQ ID NO 3
<211> LENGTH: 3147
<212> TYPE: DNA
<213> ORGANISM: Artificial Sequence
<220> FEATURE:
<223> OTHER INFORMATION: Synthetic polynucleotide

<400> SEQUENCE: 3

```
aagcttcaat gaaaaaaggg cccgcaggcc ctttgttcga tatcaatcga gattatgaca     60
acttgacggc tacatcattc acttttctt cacaaccggc acggaactcg ctcgggctgg    120
ccccggtgca ttttttaaat acccgcgaga atagagttg atcgtcaaaa ccaacattgc    180
gaccgacggt ggcgataggc atccgggtgg tgctcaaaag cagcttcgcc tggctgatac    240
gttggtcctc gcgccagctt aagacgctaa tccctaactg ctggcggaaa agatgtgaca    300
gacgcgacgg cgacaagcaa acatgctgtg cgacgctggc gatatcaaaa ttgctgtctg    360
ccaggtgatc gctgatgtac tgacaagcct cgcgtacccg attatccatc ggtggatgga    420
gcgactcgtt aatcgcttcc atgcgccgca gtaacaattg ctcaagcaga tttatcgcca    480
gcagctccga atagcgccct tccccttgcc cggcgttaat gatttgccca acaggtcgc    540 tgaaatgcgg ctggtgcgct tcatccgggc gaaagaaccc cgtattggca atatattgacg    600 gccagttaag ccattcatgc cagtaggcgc gcggacgaaa gtaaaccccac tggtgatacc    660 attcgcgagc ctccggatga cgaccgtagt gatgaatctc tcctggcggg aacagcaaaa    720
tatcacccgg tcggcaaaca aattctcgtc cctgattttt caccaccccc tgaccgcgaa    780
tggtgagatt gagaatataa cctttcattc ccagcggtcg gtcgataaaa aaatcgagat    840
aaccgttggc ctcaatcggc gttaaacccg ccaccagatg gcattaaac gagtatcccg    900 gcagcagggg atcatttgc gcttcagcca tactttcat actcccgcca ttcagagaag    960
aaaccaattg tccatattgc atcagacatt gccgtcactg cgtctttac tggctcttct   1020 cgctaaccaa accggtaacc ccgcttatta aaagcattct gtaacaaagc gggaccaaag   1080
ccatgacaaa aacgcgtaac aaaagtgtct ataatcacgg cagaaaagtc cacattgatt   1140
atttgcacgg cgtcacactt tgctatgcca tagcattttt atccataaga ttagcggatc   1200
ctacctgacg ctttttatcg caactctcta ctgtttctcc ataccgttt ttttggacat   1260 gtaggaggaa ttcacatgaa agcaaccaag ctggttctgg gtgccgtgat tctgggcagt   1320
accctgttag caggttgttc tagcaatgcc aaaatcgacc aaggcatcaa caacaatggc   1380
ccgacccacg aaaaccagct gggtgccggt gcctttggtg ttatcaggt gaaccccgtac   1440 gtgggctttg aaatgggcta tgattggctg gccgcatgc cgtacaaagg cagtgtggag   1500
aacggcgcct ataaagcaca gggcgtgcag ctgacagcaa aactgggcta cctattacc   1560 gacgacctgg acatctacac acgcttaggc ggcatggtgt ggcgcgccga taccaagagc   1620
```

```
aacgtgtacg gcaagaacca cgataccggc gtgagtccgg tgtttgccgg cggtgtggag   1680
tatgcaatca ccccggaaat tgccacacgt ggaattgcta gcggtacccc cggggccgag   1740
gccggcatca ccggcacctg gtacaaccag ctcggctcga ccttcatcgt gaccgcgggc   1800
gccgacggcg ccctgaccgg aacctacgag tcggccgtcg gcaacgccga gagccgctac   1860
gtcctgaccg gtcgttacga cagcgccccg gccaccgacg gcagcggcac cgccctcggt   1920
tggacggtgg cctggaagaa taactaccgc aacgcccact ccgcgaccac gtggagcggc   1980
cagtacgtcg gcggcgccga ggcgaggatc aacacccagt ggctgctgac ctccggcacc   2040
accgaggcca acgcctggaa gtccacgctg gtcggccacg acaccttcac caaggtgaag   2100
ccgtccgccg cctccatcta gtgactgtat aaaaccacag ccaatcaaac gaaactcgag   2160
cgatcggacg tcccaggcta tactcaagcc tggttttttg atggctgcag catatgtcta   2220
gacgtatttt acactttatg cttccggctc gtataatgtg tggaattgtg agcggataac   2280
aatttcacac aggagacagc tatggtgagc aagggcgagg agctgttcac cggggtggtg   2340
cccatcctgg tcgagctgga cggcgacgta acgccacca agttcagcgt gtccggcgag   2400
ggcgagggcg atgccaccta cggcaagctg accctgaagt tcatctgcac caccggcaag   2460
ctgcccgtgc cctggcccac cctcgtgacc accctgacct acggcgtgca gtgcttcagc   2520
cgctaccccg accacatgaa gcagcacgac ttcttcaagt ccgccatgcc cgaaggctac   2580
gtccaggagc gcaccatctt cttcaaggac gacggcaact acaagacccg cgccgaggtg   2640
aagttcgagg gcgacaccct ggtgaaccgc atcgagctga agggcatcga cttcaaggag   2700
gacggcaaca tcctggggca caagctggag tacaactaca acagccacaa cgtctatatc   2760
atggccgaca agcagaagaa cggcatcaag gtgaacttca gatccgccca acatcgag   2820 gacggcagcg tgcagctcgc cgaccactac cagcagaaca cccccatcgg cgacggcccc   2880
gtgctgctgc ccgacaacca ctacctgagc acccagtccg ccctgagcaa agaccccaac   2940
gagaagcgcg atcacatggt cctgctggag ttcgtgaccg ccgccgggat cactctcggc   3000
atggacgagc tgtacaagta acaaagcccg aaaggaagct gagttggctg ctgccaccgc   3060
tgagcaataa cctagggtcg acgagctcct agcataaccc cttggggcct ctaaacgggt   3120
cttgaggggt ttttgtcta caagctt                                       3147

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4
caatgaaaaa agggcccgca                                              20

<210> SEQ ID NO 5
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 5
tcttccgctt cctcgctca                                               19

<210> SEQ ID NO 6
<211> LENGTH: 21
```

```
-continued

<212> TYPE: DNA
<213> ORGANISM: Artificial Sequence
<220> FEATURE:
<223> OTHER INFORMATION: Synthetic polynucleotide

<400> SEQUENCE: 6
cgtcgtcgtc gtcgtcgatc g                                          21

<210> SEQ ID NO 7
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 7
cgatcgcgtc gtcgtcgtcg tcgtcgtcgt cgtcgt                          36
```

METHODS OF DETECTION OF COMPOUND, ANTIBODY OR PROTEIN USING RECOMBINANT ENDOSPORES OR BACTERIA AS SENSING ELEMENT

This is a continuation of U.S. application Ser. No. 16/813,028, filed Mar. 9, 2020, the contents of which is incorporated herein by reference in its entirety.

FIELD OF THE INVENTION

The present invention relates to a novel method of detecting the presence of an analyte in a sample using recombinant spores or bacteria expressing recombinant proteins on the surface of the spores or the bacteria and detection systems using such recombinant spores or bacteria.

BACKGROUND OF THE INVENTION

Display of proteins and peptides on the surface of microbes is becoming a fundamental tool to overcome problems in bioprocesses, harsh industrial processes, vaccine development, and environmental protection (Kim and Schumann, 2009). Surface display requires expression of a target protein on the surface of the cell membrane of living cells through genetic engineering techniques. For successful display, the target protein needs to be fused with an anchor protein (Van Bloois et al., 2011) in order to display translocated-incompatible and multimeric proteins (Kim and Schumann, 2009). The first surface display system was developed by George P. Smith et al. in 1985, wherein antibodies were expressed on the surface of phages using filamentous bacteriophage M13. Said system provides a new technique for antigen production (Smith, G. P., 1985). The surface display technique has since been applied to other organisms such as bacteria, yeasts and spores.

Extensive studies have been performed with respect to surface display systems in Gram-negative bacteria. Among those, *Escherichia coli* (*E. coli*) has been widely studied, and found to display heterologous proteins on the cell surface (Francisco 1992, Georgiou 1996). Professor George Georgiou's group constructed a fusion protein containing (i) the signal sequence and first nine N-terminal amino acids of the mature lipoprotein, an outer membrane protein of *E. coli*, (ii) the amino acids 46-159 of OmpA, another outer membrane protein of *E. coli*, and (iii) the complete β-lactamase. It was demonstrated that this fusion protein is expressed outside of *E. coli* and exhibits β-lactamase activity (Francisco 1992, Georgiou 1996). Surface display of *E. coli* has a variety of different applications, such as whole-cell biocatalysts, biosorbents, peptide screening, vaccine production, and antibody production (Nguyen 2014).

Compared with systems in other organisms, surface display on spores has advantages in terms of high stability, easy purification and recovery and the ability to express large molecules. Due to intracellular production, spores are advantageous compared with non-spore producers in view of the fact that heterologously anchored proteins cannot cross any membrane. Moreover, because of a rigid spore coat, proteins and enzymes displayed on spores become resistant to harsh conditions during industrial procedure such as high temperature, chemicals and radiation; they can also be stored for a long time at room temperature (Kim and Schumann, 2009).

*Bacillus subtilis* is an aerobic, Gram-positive bacterium. It widely exists in soil, lakes, oceans, animals and plants. While *Bacillus subtilis* has been found in human intestine, it is non-pathogenic. The most commonly used strains of *Bacillus subtilis* in laboratories are strains 168, PY79, W23 and NCIB3610, of which the genome of strain 168 has been completely sequenced. The size of *Bacillus subtilis* is about 0.7 to 0.8×3 µm; it has no capsule, has flagella all over the surface, and is mobile.

Under extreme conditions, *Bacillus subtilis* has the ability to enter sporulation and survive for a long time under harsh environmental conditions. At first, the cells divide to produce smaller prespores and larger mother cells, which are separated by a membrane in between. In the next stage, the mother cells phagocytose the prespores, and the surface of the prespores produces a peptidoglycan cortex and spore coat. The prespores are then released from the mother cells after maturation (Mohab A. Al-Hinai, et al., 2015). Spores are of a complex multi-layer structure, which consists mainly of four layers: the innermost core containing the important genetic material, DNA, which is surrounded by the inner membrane; the peptidoglycan cortex with peptidoglycan as the main component; the spore coat composed of several layers of proteins including basement layer, inner coat, outer coat, and crust; and the exosporium (Setlow, P., 2014; Henriques et al., 2004).

*Bacillus subtilis* spores contain at least 70 different spore coat proteins including CotA, CotB, CotC, CotD, CotE, CotF, CotG, CotH CotJA, CotJC, CotM, CotS, CotSA, CotT, CotX, CotY, CotZ, SpoIVA, SpoVID, YabG, and YrbA (McKenney et al., 2013; Takamatsu and Watabe, 2002), but the most preferred anchored proteins are the outer coat proteins.

A number of factors affect the efficiency of *Bacillus subtilis* spore surface display systems, including anchor proteins, target proteins, linkers, expression vectors and other experimental parameters. In recent years, many anchor proteins have been reported for use in *Bacillus subtilis* spore surface display, including CotB, CotC, CotG, CotZ, CotX, CotY, CotA, OxdD, CotE, CotZ, CgeA and other coat proteins. Of these, CotB, CotC and CotG have been studied in depth. CotB was the first spore coat protein to be used in spore surface display technology, and different lengths of CotB have worked as anchor proteins to successfully locate exogenous proteins on the spore surface (Isticato R. et al., 2001). Linker peptides can form stable helical structures to solve the problem of having a rigid structure between the anchor protein and target protein. Substantial research has shown that inclusion of flexible linker peptides in constructing a recombinant vector is an effective way to regulate the function of fusion enzymes. Fusion of exogenous and anchor proteins can be achieved by involving the N-terminal, C-terminal and sandwich structures of the proteins. The fusion method is determined through the direction of anchoring during the process of sporulation, which locates a target protein on the spore surface being expressed with anchor proteins. *Bacillus subtilis* spore surface display can be conducted by recombinant and nonrecombinant fusion approaches (Isticato R, Ricca E., 2014). The method of recombination is mostly based on fusion of the genes encoding the foreign and anchor proteins, using either integrated or episomal plasmids. Along with the induction of the spore formation process, foreign proteins are successfully displayed on the spore surface without affecting the structure and function of the spores.

Enzyme-linked immunosorbent assay (ELISA) was developed by Engvall and Perlmann in 1971 (Engvall and Perlmann 1972), and has thereafter been widely used to detect proteins, antibodies, and compounds. It utilizes antibodies against an analyte to detect the same in a sample, and conjugates an enzyme (such as horseradish peroxidase (HRP)) to one of the antibodies, which reacts with its substrate and generates a detectable signal to quantify the analyte to be tested (Lequin 2005). ELISA is an important rapid screening diagnostic tool in biotechnology.

The most common type of ELISA is sandwich ELISA, wherein two antibodies from different species are used to bind to different parts of an analyte (Schmidt, 2012). Said method is of excellent specificity and high reliability. In this method, an antibody from species A, serving as a capture antibody, is attached to a solid surface. Afterward, a sample is added so that an existing antigen binds to the capture antibody, followed by addition of an antibody from species B as a detecting antibody which also binds to the antigen. A secondary antibody specifically binding to the antibody from species B is then added; said secondary antibody is linked to an enzyme. Finally, the substrate of the enzyme is added, and the reaction thereof produces a detectable signal. The mostly commonly used signal is color change. Others include fluorescence or electrochemical signals.

Another commonly used ELISA is competitive ELISA, which is applicable to compounds (haptens) (Chittamma 2013). Since they are too small to be bound by two different antibodies, sandwich ELISA is not suitable for compounds. Competitive ELISA may be performed in different ways. In one method, a compound is first attached to the bottom of a well, wherein the structure thereof is similar or identical to that of the test compound. The test compound and an antibody are mixed in another test tube. After a period of time, the mixture is added to the above well. At this point, the test compound competes with the compound at the bottom of the well for the antibody. The well is then washed to remove the antibody that fails to bind to the compound at the bottom of the well. The greater the amount of test compounds, the smaller the amount of antibodies that remain in the well. Secondary antibody linked with an enzyme is then added, and the reaction produces a detectable signal. The greater the amount of test compounds, the weaker the signal.

Lateral flow assay (LFA) is a paper-based platform for the detection and quantification of analytes in complex mixtures, where the sample is placed on a test device and the results are typically displayed within 5-30 min. Low development costs and ease of production of LFA have resulted in the expansion of its applications to multiple fields in which rapid tests are required. LFA-based tests are widely used in hospitals, physicians' offices and clinical laboratories for qualitative and quantitative detection of specific antigens and antibodies. A variety of biological samples can be tested using LFAs, including urine, saliva, sweat, serum, plasma, whole blood and other fluids. Further industries in which LFA-based tests are employed include veterinary medicine, quality control, product safety in food production, and environmental health and safety. In these areas of utilization, rapid tests are used to screen for animal diseases, pathogens, chemicals, toxins and water pollutants, among others.

The principle behind LFA is simple: a liquid sample (or its extract) containing the analyte of interest moves without the assistance of external forces (capillary action) through various zones of polymeric strips, on which molecules that can interact with the analyte are attached. A typical lateral flow test strip consists of overlapping membranes that are mounted on a backing card for better stability and handling. The sample is applied at one end of the strip, on the adsorbent sample pad, which is impregnated with buffer salts and surfactants that make the sample suitable for interaction with the detection system. The sample pad ensures that the analyte present in the sample will be capable of binding to the capture reagents of conjugates and on the membrane. The treated sample migrates through the conjugate release pad, which contains antibodies that are specific to the target analyte and are conjugated to colored or fluorescent particles—most commonly colloidal gold and latex microspheres. The sample, together with the conjugated antibody bound to the target analyte, migrates along the strip into the detection zone. This is a porous membrane (usually composed of nitrocellulose) with specific biological components (mostly antibodies or antigens) immobilized in lines. Their role is to react with the analyte bound to the conjugated antibody. Recognition of the sample analyte results in an appropriate response on the test line, while a response on the control line indicates the proper liquid flow through the strip. The read-out, represented by the lines appearing with different intensities, can be assessed by eye or using a dedicated reader. The liquid flows across the device because of the capillary force of the strip material and, to maintain this movement, an absorption pad is attached at the end of the strip. The role of the absorption pad is to wick the excess reagents and prevent backflow of the liquid.

Flow cytometry (FCM) is an analytical technique for measuring suspended cells or particles in liquid phase. It can quickly detect and analyze various physical properties of a single particle, such as particle size, density, internal structure, and relative fluorescence intensity. The characteristics of cells can be obtained by recording the scattered light signals and fluorescent signals of the cells by the photoelectric system. Particles or cells having a diameter of 0.2 to 150 μm in a suspension are suitable for use in flow cytometry (Rowley, T, 2012). Flow cytometry is widely used in various research fields, such as molecular biology, pathology, immunology, botany, and marine biology.

Flow cytometric sorting permits the selection, enrichment, apportionment, or division of populations of cells, viruses, bodies or particles of interest. The selection criteria include measurable properties of individual cells that can be detected from outside the cell, with or without the aid of chemical reagents or of complexes or bodies that are, or that may be caused to be, associated with the cell. For instance, properties of cells may be measured or approximated by detecting and/or quantifying the association of the cells with one or more labels, such as molecules, complexes, or bodies that fluoresce or have been modified to be rendered fluorescent. Such fluorescent molecules, complexes, and/or bodies may differentially associate with cells on the basis of qualitative or quantitative properties of the cells, including their composition with respect to proteins, lipids, phosphoproteins, glycoproteins, phospholipids, glycolipids, nucleic acids (including the quantity, sequence, or organization of nucleic acids), carbohydrates, salts/ions, and any other molecules in, on, or associated with the cells. Further, such fluorescent molecules, complexes, and/or bodies may differentially associate with cells based on physical or physiological characteristics of the cells, examples of which include but are not limited to membrane permeability, membrane composition, membrane fluidity, chemical or membrane potential, viability, chemical gradients, motility, reduction of oxidation potential or state, and other parameters or properties.

Whole cell-based biosensors are inexpensive and easy to operate, and serve as an alternative for fast screening (Bereza-Malcolm et al., 2015; Mehta et al., 2016). In said method, a synthetic gene is incorporated into a cell, wherein a specific compound is targeted, and an easily detectable signal is produced (Liu et al., 2014; Tian et al., 2017). For example, chemical activated luciferase gene expression (calux) can be used to detect specific chemicals (Sany et al., 2016). The cell contains luciferase gene and its regulatory DNA. After the chemical substance to be tested binds to its corresponding receptor protein, the complex links to the regulatory DNA and induces expression of luciferase. Calux has been used to detect dioxin (Sany et al., 2016; Xu et al., 2018), bisphenol A (Dusserre et al., 2018), heterocyclic aromatic amines (Steinberg et al., 2017) and other compounds. For dioxin, the detection takes approximately 24 hours (excluding sample preparation time), and the detection limit is 1 pM (Sany et al., 2016).

Avidin is a protein derived from both avians and amphibians that shows considerable affinity for biotin, a co-factor that plays a role in multiple eukaryotic biological processes. Avidin and other biotin-binding proteins, including streptavidin and neutravidin proteins, have the ability to bind up to four biotin molecules. The avidin-biotin complex is the strongest known non-covalent interaction ($Kd=10^{-15}$ M) between a protein and a ligand. The bond formation between biotin and avidin is very rapid, and once formed, is unaffected by extremes of pH, temperature, organic solvents or other denaturing agents. These features of biotin and avidin—features that are shared by streptavidin and neutravidin—are useful for purifying or detecting proteins conjugated to either component of the interaction.

Haptens are small-molecular-weight compounds that evoke an immune response only when they are attached to carrier proteins. In vivo, haptens readily bind to serum proteins such as albumin. The combined molecular weights of albumin and the hapten need to exceed 3000 MW to stimulate the immune system. The immune response is directed at both the hapten and the carrier protein. Commonly known haptens include biotin, parathion-methyl, dioxin, ractopamine, melamine and various toxic drugs.

Analytical techniques such as gas (or liquid) chromatography-mass spectrometry (GC-MS), and high performance liquid chromatography (HPLC) are the most common methods to detect compounds, antibodies and/or proteins. Although these methods are sensitive and accurate, complex procedures, high equipment costs, and intensive personnel training restrict their use. At present, rapid screening methods for compounds, antibodies and/or proteins include enzyme-linked immunosorbent assay (ELISA) and lateral flow assay (LFA). Both methods are relatively inexpensive and fast. However, it would be desirable if the detection limit of the above methods can be further improved.

SUMMARY OF THE INVENTION

In the present invention, recombinant spores or bacteria are used as a sensing element in ELISA, LFA, flow cytometry and other methods. This detection method has several advantages, such as easier handling, lower cost, and lower detection limit/higher sensitivity.

Therefore, the present invention provides a method and a system for detecting the presence of an analyte in a sample. In particular, the present invention provides a system, such as a diagnostic kit, for detecting the presence of an analyte in a sample comprising (a) a recombinant bacterium or spore expressing one or more recombinant protein on the surface thereof, wherein the recombinant protein specifically binds to the analyte directly or through a binding agent that specifically binds to the recombinant protein and the analyte, and (b) a signal-producing substance that can be detected.

In one aspect, the analyte is a compound, an antibody or a protein.

In one embodiment, the one or more recombinant proteins expressed by the recombinant bacteria or on the surface of the recombinant spore comprise a protein selected from streptavidin, avidin, enhanced green fluorescent protein (eGFP), green fluorescent protein (GFP), red fluorescent protein (RFP), yellow fluorescent protein (YFP), catalase, laccase, beta-galactosidase, luciferase, beta-lactamase, a protein specifically or non-specifically binding to the analyte or binding agent, an antibody, an antigen, protein A, protein G, protein L, and protein A/G, preferably eGFP and/or streptavidin.

In another embodiment, the recombinant protein is a fusion protein, wherein said fusion protein preferably comprises a coat protein of the recombinant spore and an exogenous protein or a membrane protein (or an artificial membrane protein) of the recombinant bacterium and an exogenous protein, wherein said exogenous protein is preferably streptavidin, avidin, protein A, protein G, protein L, or/and protein A/G.

In still another embodiment, the recombinant spore is produced by *Bacillus* species, preferably *Bacillus subtilis*, more preferably a strain of *Bacillus subtilis* selected from strains 168, PY79, W23 and NCIB3610. In a preferred embodiment, the fusion protein expressed by the recombinant spore comprises a coat protein selected from CotA, CotB, CotC, CotE, CotG, Cotta CotX, CotY and CotZ.

In one aspect, the recombinant bacteria are derived from *Escherichia coli, Bacillus subtilis, Staphylococcal aureus, Staphylococcal xylosus, Staphylococcal carnosus, Neisseria gonorrhoeae, Salmonella enterica, Lactococcus lactis*, or *Streptococcus gordonii*, preferably *Escherichia coli*.

In another aspect, the binding agent is an antibody against the analyte, preferably an antibody conjugated with biotin or other protein-binding molecules.

In a further aspect, the signal-producing substance comprises dye, fluorescent dye, fluorescent protein, colloidal gold nanoparticles, nanoparticles with color, or enzymes capable of converting a substrate providing no signal to a substrate providing a signal. In another embodiment, the signal-producing substance is a detecting agent for detecting the binding of the recombinant protein or binding agent to the analyte. In one embodiment, the detecting agent is an antibody or an antigen which specifically binds to the analyte.

In a further aspect, the system further comprises a competing agent that competes for the binding of the analyte to the recombinant protein or binding agent. In one embodiment, the competing agent comprises a signal-producing substance.

In yet another aspect, the system further comprises (a) a membrane with a positive region and a negative region, wherein antibodies, antigens or competing agents are immobilized in the positive region and/or the negative region for detecting presence or absence of analyte in the sample; or (b) an ELISA plate with proteins capable of binding to the analyte, antibodies, antigens, or competing agents immobilized therein, for detecting presence or absence of analyte in the sample. Preferably, said membrane is a nitrocellulose membrane commonly used in lateral flow assays.

In a preferred aspect, the binding of the recombinant protein to the analyte is detected by flow cytometry, lateral flow, or ELISA.

The present invention further provides a method of detecting an analyte in a sample using the above system.

DETAILED DESCRIPTION

Definitions

Figure 1:
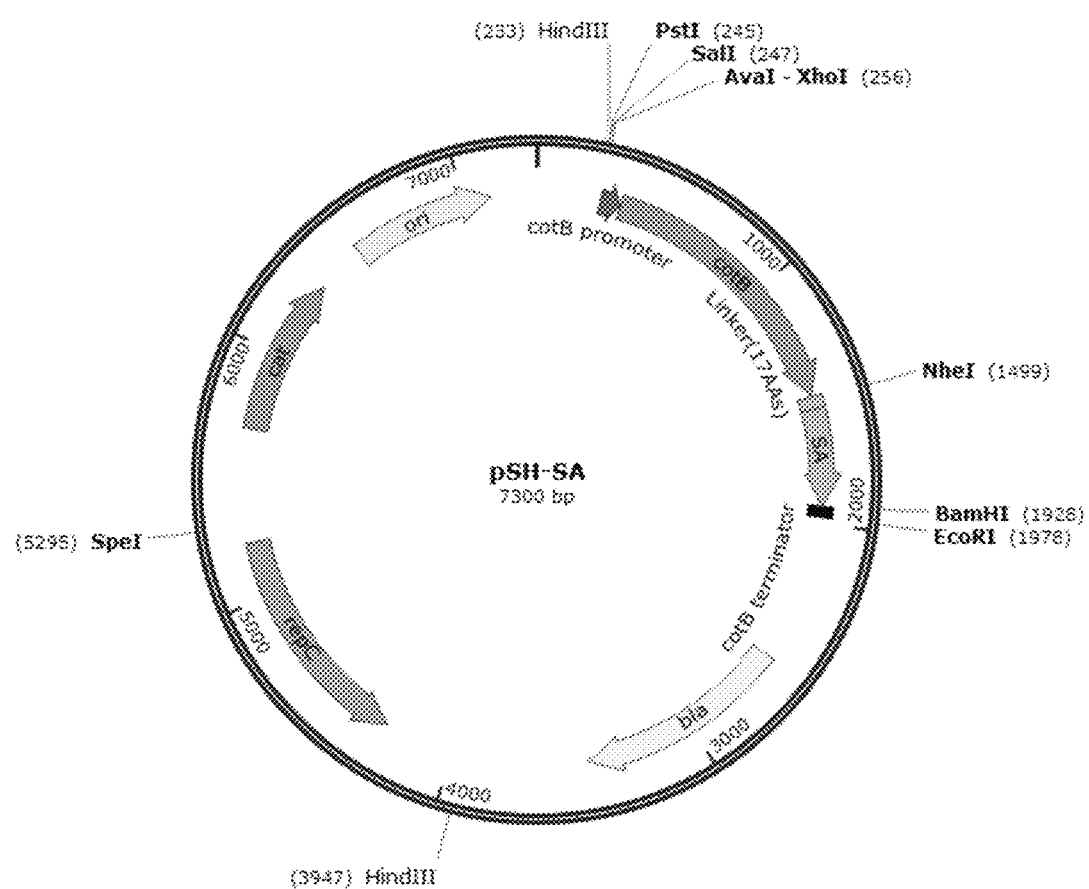
FIG. 1 shows the plasmid map of pSH-SA.

Unless defined otherwise, technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "analyte" as used herein refers to a substance to be detected for presence or absence in a sample, which can be a compound, an antibody, or a protein.

The term "bacterium" or "bacteria" refers to all Gram-positive and Gram-negative bacteria, including but not limited to Escherichia coli, Bacillus subtilis, Staphylococcal aureus, Staphylococcal xylosus, Staphylococcal carnosus, Neisseria gonorrhoeae, Salmonella enterica, Lactococcus lactis, and Streptococcus gordonii.

The term "recombinant" refers to polynucleotides synthesized or otherwise manipulated in vitro ("recombinant polynucleotides") and to methods of using recombinant polynucleotides to produce gene products encoded by those polynucleotides in cells or other biological systems. For example, a cloned polynucleotide may be inserted into a suitable expression vector, such as a bacterial plasmid, and the plasmid can be used to transform a suitable host cell. A host cell that comprises the recombinant polynucleotide is referred to as a "recombinant host cell" or a "recombinant bacterium." The gene is then expressed in the recombinant host cell to produce, e.g., a "recombinant protein/polypeptide."

The term "spore" includes any spore commonly used to monitor sterilization processes and endospores. For example, spores from Bacillus subtilis, Bacillus circulans, Clostridium perfringens, Clostridium sporogenes or Bacillus stearothermophilus are useful. Spores from Bacillus subtilis strains 168, PY79, W23 and NCIB3610 are particularly useful. The spores can be unpurified or purified. For example, B. subtilis spores can be separated into heavy and light spores by differential centrifugation of an aqueous suspension. Heavy spores pellet after centrifugation for 12 to 15 minutes at 2,000×g, whereas the light spores remain in suspension. The light spores can be pelleted by centrifugation of the supernatant from the first centrifugation for 30 minutes at 2,000×g. The heavy spores can be further purified by filtering a dilute suspension of heavy spores through WhatmanGF/D glass fiber filters to remove bits of agar, denatured nucleoproteins and other debris that sediments with the spores in the first centrifugation.

The term "exogenous" as used herein means derived from outside the host strain and the term "exogenous proteins" includes proteins, peptides, and polypeptides.

The "recombinant protein" expressed by the recombinant bacterium or spore of the present invention comprises a protein selected from (but not limited to) streptavidin, avidin, enhanced green fluorescent protein (eGFP), green fluorescent protein (GFP), red fluorescent protein (RFP), yellow fluorescent protein (YFP), catalase, laccase, beta-galactosidase, luciferase, beta-lactamase, a protein specifically or non-specifically binding to the analyte or binding agent, an antibody, an antigen (preferably specific to the analyte), protein A, protein G, protein L, and protein A/G.

The term "coat protein" is used herein in the broadest sense and includes any native protein present in the outer layer of spore coat and exposed on the spore surface, and functional fragments and functional amino acid sequence variants of such native proteins. The term includes native coat protein sequences of any spore-forming species and subspecies of the genus Bacillus, and functional fragments and functional amino acid sequence variants of such native coat protein sequences. The term "native" in this context is used to refer to native-sequence polypeptides, and does not refer to their origin or mode of preparation. Thus, native coat proteins may be isolated from their native source but can also be prepared by other means, e.g. synthetic and/or recombinant methods. Functional amino acid sequence variants include chimeric variants, comprising fusions of two or more native externally exposed spore coat protein sequences, or fragments thereof. Preferred coat proteins include CotA, CotB, CotC, CotE, CotG, CotW, CotX, CotY and CotZ.

The terms "spore coat protein B" and "CotB protein" are used interchangeably, and refer to externally exposed spore coat proteins that are characterized by a highly hydrophobic region at the C-terminus, and classified as CotB, such as CotB1 or CotB2 proteins based on sequence homologies. Preferably, the CotB proteins herein show significant amino acid sequence identity to each other and to the amino terminal two-thirds of the 42.9-kDa component of the B. sublilis spore coat associated with the outer coat layer. The sequence of a representative CotB protein herein is shown in SEQ ID NO: 1, which is specifically included within the definition of spore coat protein B (CotB) herein.

The terms "variant" and "amino acid sequence variant" are used interchangeably, and include substitution, deletion and/or insertion variants of native sequences. In a preferred embodiment, the protein variants have at least about 80% amino acid sequence identity, or at least about 85% amino acid sequence identity, or at least about 90% amino acid sequence identity, or at least about 92% amino acid sequence identity, or at least about 95% amino acid sequence identity, or at least about 95% amino acid sequence identity, or at least about 98% amino acid sequence identity with a native sequence.

A "functional" fragment or variant retains the ability to be propagated and stably displayed on the surface of a spore, such as a *Bacillus* spore.

The term "protein expression on the surface" is used herein in the broadest sense and includes complete and partial exposure of a protein, such as a spore coat protein or a recombinant protein.

The term "fusion" is used herein to refer to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

The term "compound" refers to a chemical compound, such as biotin, dioxin, digoxin, and other protein-binding or antibody-binding chemicals.

The terms "polypeptide," "peptide" and "protein" are used interchangeably herein to refer to a polymer of amino acid residues. The terms apply to amino acid polymers in which one or more amino acid residues are an artificial chemical analogue of a corresponding naturally occurring amino acid, as well as to naturally occurring amino acid polymers. Amino acids may be referred to herein by either their commonly known three letter symbols or the terminology recommended by Nomenclature Commission. Nucleotides, likewise, may be referred to by their commonly accepted single-letter codes, i.e., the one-letter symbols recommended by the IUPAC-IUB.

"Polynucleotide" and "nucleic acid" refer to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs. It will be understood that, where required by context, when a nucleotide sequence is represented by a DNA sequence (i.e., A, T, G, C), this also includes an RNA sequence (i.e., A, U, G, C) in which "U" replaces "T."

As used herein, an "antibody" refers to a protein comprising one or more polypeptides substantially or partially encoded by immunoglobulin genes or fragments of immunoglobulin genes. The term antibody is used to mean whole antibodies and binding fragments thereof. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 KDa) and one "heavy" chain (about 50-70 KDa). The N-terminus of each chain defines a variable region of about 100 to 110 or more amino acids primarily responsible for antigen recognition. The terms variable light chain (VL) and variable heavy chain (VH) refer to these light and heavy chains, respectively. In the present application, the term "antibody" specifically covers, without limitation, monoclonal antibodies, polyclonal antibodies, and antibody fragments.

An "antigen" refers generally to a substance capable of eliciting the formation of antibodies in a host or generating a specific population of lymphocytes reactive with that substance. Antigens may comprise macromolecules (e.g., polypeptides, proteins, and polysaccharides) that are foreign to the host.

The term "binding agent" refers to an agent that specifically binds to the recombinant protein expressed by the recombinant bacteria or on the surface of the recombinant spore and the analyte to be detected so that the recombinant protein and the analyte are indirectly connected or linked. For example, the binding agent can be an antibody against the analyte. Preferably, the antibody is conjugated with biotin, digoxin or other protein-binding molecules. In one embodiment, the above protein-binding molecules bind to the binding partners thereof expressed by the recombinant spore or bacteria through specific protein-protein interactions. Alternatively, the antibody may be bound by a recombinant protein expressed by the recombinant spore or bacteria through the constant region thereof.

The term "biotinylation" refers to the process of attaching biotin to proteins and other macromolecules (Barat and Wu, 2007).

The terms "specific binding" and "specifically binds" when used in reference to the interaction of an antibody and a protein or peptide mean that the interaction is dependent upon the presence of a particular structure (i.e., for example, an antigenic determinant or epitope) on a protein; in other words an antibody is recognizing and binding to a specific protein structure rather than to proteins in general. For example, if an antibody is specific for epitope "A," the presence of a protein containing epitope A (or free, unlabeled A) in a reaction containing labeled "A" and the antibody will reduce the amount of labeled A bound to the antibody.

The term "detecting agent" refers to an agent used for detecting the direct or indirect binding between the recombinant protein expressed by the recombinant bacteria or on the surface of the recombinant spore or the binding agent and the analyte to be detected. Preferably, the detecting agent is an antibody or an antigen which specifically binds to the analyte. More preferably, the detecting agent includes a primary antibody specific for the analyte to be detected and a secondary antibody specific for the primary antibody. In one embodiment, the detecting agent comprises a signal-producing substance. Such detection may be performed with techniques commonly known in the art, including but not limited to flow cytometry, lateral flow assay, and ELISA.

The term "signal-producing substance" refers to a substance providing a signal that can be detected by eye or detectors such as a fluorescence microscope. Such signal-producing substance includes, but not limited to, a dye, fluorescent dye, fluorescent protein, colloidal gold nanoparticles, nanoparticles with color, or enzymes capable of converting a substrate providing no signal to a substrate providing a signal. The signal-producing substance may be a detecting agent for detecting the binding of the recombinant protein or binding agent to the analyte.

The term "competing agent" refers to an agent that competes with the analyte for binding to the recombinant protein or binding agent. For example, the competing agent may be the same as the analyte (such as a compound) except that it is labeled with a fluorescence substance so as to become a signal-producing substance, or that it is linked with a carrier protein.

The term "carrier protein" refers to an immunogenic protein or peptide containing enough amino acid residues in the reactive side chains to conjugate with the target compound. The carrier protein may be selected from (but not limited to) the following: bovine serum albumin (BSA), serum globulin, albumins, ovalbumin and many others. Synthetic polypeptides such as poly-L-glutamic acid can also be used.

The term "label" or "labeled with" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads), fluorescent dyes (e.g., fluorescein, Texas Red, rhodamine, green fluorescent protein, and the like), radiolabels (e.g., 3 H, 125 1, 35 S, 14 C, or 32 P), enzymes (e.g., horse radish peroxidase (HRP), alkaline phosphatase and others commonly used in an ELISA), and calorimetric labels such as colloidal gold nanoparticles or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241 (all herein incorporated by reference). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

The term "flow cytometry" refers to a technique which quantifies and/or sorts a target substance through detecting fluorescence signal labeled in or on a single cell or small particle in a solution by an optical or electronic detector.

The term "lateral flow assay" refers to an assay in which detection is based on the specificity and immunoaffinty between an antigen and an antibody, using colloidal gold as a color developing agent. In an example of such assay, an antibody against the target substance is first immobilized in the test line on a nitrified cellulose membrane and a secondary antibody against the above antibody against the target substance is immobilized in the control line on the membrane; a colloidal gold particle and another antibody against the target substance are then conjugated and immobilized on a conjugated release pad. When a sample contains the target substance, the colloidal gold-antibody against the target substance conjugate on the conjugated release pad will bind the target substance, and once the complex reaches the test line, the antibody against the target substance in the test line will bind the above complex and lead to color development. The secondary antibody immobilized in the control line can bind the colloidal gold-antibody against the target substance conjugate and serves as a positive control. In the present invention, antibodies, antigens or competing agents may be immobilized in the positive region and/or the negative region for detecting the presence or absence of an analyte in the sample. For example, one or more substances selected from the following may be immobilized in the positive or negative region on the membrane: antibodies against the analyte, the carrier protein, the spore, the recombinant protein on the spore or the binding agent; competing agents; and antigens recognized by the analyte.

The term "ELISA" refers to an assay using a plate with an antibody against the target substance immobilized. When a sample contains the target substance, the target substance binds to the antibody on the ELISA plate through the specificity between the antibody and the target substance. Another antibody against the target substance conjugated with an enzyme is then added to the plate. When said antibody binds to the target substance, the enzyme conjugated thereon will catalyze the substrate thereof and the chemical reaction leads to color development, which is then measured for absorbance so that the concentration of the target substance in the sample can be calculated. In the present invention, proteins capable of binding to the analyte, antibodies, antigens, or competing agents may be immobilized on the ELISA plate for detecting presence or absence of analyte in the sample. For example, the above antibodies are those against the carrier protein or the analyte (such as a protein); the above proteins capable of binding to the analyte are proteins that bind to the target antibody through its constant region; and the above antigens are those recognized by the target antibody.

The present invention provides a system for detecting the presence of an analyte in a sample, comprising (a) a recombinant bacteria or spore expressing one or more recombinant proteins on the surface thereof, wherein at least one of the recombinant proteins specifically binds to the analyte directly or through a binding agent that specifically binds to the recombinant protein and the analyte, and (b) a detecting agent for detecting the binding of the recombinant protein or binding agent to the analyte. In a preferred embodiment, the analyte is a compound, an antibody or a protein in a sample, as discussed below, taking spores as an example.

Detection by Flow Cytometry

The detection system of the present invention can be used to detect the presence of an analyte in a sample through flow cytometry. For example, when the analyte is biotin or a biotinylated compound, detection of the same is performed through a recombinant spore expressing streptavidin or avidin on the surface and competitive binding with the recombinant spore between biotin or the biotin moiety of the biotinylated compound in the sample and fluorescein-labeled biotin added to the reaction.

In another embodiment, the recombinant protein expressed by the recombinant spore comprises an exogenous protein specifically binding to a target compound. A target compound conjugated with a fluorescence substance (f-target) is used as a signal-producing competing agent to compete with the target compound in the sample for binding to the recombinant protein. Alternatively, an anti-target compound antibody is optionally conjugated with biotin or other protein-binding molecules to serve as a binding agent. In this case, the recombinant protein comprises streptavidin/avidin, proteins specifically binding to the above protein-binding molecules, or protein A, protein G, protein L, protein A/G or other antibody binding proteins capable of binding to the constant region of the above anti-target compound antibody. The anti-target compound antibody may also be displayed on the surface of the spore in the form of a fusion protein.

When the analyte is an antibody, the recombinant protein expressed by the recombinant spore comprises an antigen recognized by the target antibody. The signal-producing detecting agent is an antibody, protein A, protein G, protein L, or protein A/G capable of binding to the constant region of the target antibody conjugated with a fluorescence substance. In one embodiment, the recombinant protein expressed by the recombinant spore comprises an antibody, protein A, protein G, protein L, or protein A/G capable of binding to the constant region of the target antibody. The signal-producing detecting agent is an antigen recognized by the target antibody conjugated with a fluorescence substance. Alternatively, an antibody capable of binding to the constant region of the target antibody optionally conjugated with biotin or other protein-binding molecules may be used as a binding agent. In this case, the recombinant protein comprises streptavidin/avidin, proteins specifically binding to the above protein-binding molecules, or protein A, protein G, protein L, protein A/G or other antibody binding proteins capable of binding to the constant region of the antibody against the target antibody.

When the analyte is a protein, an anti-target protein antibody is optionally conjugated with biotin or other protein-binding molecules to serve as a binding agent. The recombinant protein expressed by the recombinant spore comprises streptavidin/avidin, proteins specifically binding to the above protein-binding molecules, or an antibody, protein A, protein G, protein L, protein A/G or other antibody binding proteins capable of binding to the constant region of the above anti-target protein antibody. Alternatively, the anti-target protein antibody is displayed on the surface of the spore in the form of a fusion protein. Another anti-target protein antibody is conjugated with a fluorescence substance or linked with an antibody against itself (which is fluorescently labeled) to serve as a signal-producing detecting agent.

Detection by Lateral Flow Assay

The detection system of the present invention can be used to detect the presence of an analyte in a sample through lateral flow assay using a detecting agent labeled with dyes, fluorescent dyes, fluorescent proteins, colloidal gold nanoparticles, nanoparticles with color, or enzymes which can convert a substance providing no signal to a substance providing signal.

In one embodiment, the detecting agent is labeled with gold nanoparticles. In one embodiment, the gold nanoparticles are conjugated to an anti-spore antibody to form an AuNP-Ab complex.

When the analyte is a compound, the recombinant protein expressed by the recombinant spore comprises a target-binding protein specifically binding to the target compound. The AuNP-Ab complexes (as a signal-producing substance) and the spores are mixed to form AuNP-Ab-spore complexes. The target compound and a carrier protein are linked to form a carrier-target, which serves as a competing agent. Anti-carrier antibodies are immobilized in the negative region on the membrane, and anti-spore antibodies or antibodies against the recombinant protein are immobilized in the positive region on the membrane (said antibodies and the antibodies conjugated with AuNP bind to different epitopes on the spore), wherein the negative region is closer to the sample introduction site on the membrane, and the positive region is closer to the absorption pad on the membrane. The sample, the above AuNP-Ab-spore complex, and the carrier-target are then mixed so that competition can occur between the target compound contained in the sample and the competing agent for binding to the AuNP-Ab-spore complex. Alternatively, the above competing agent is immobilized in the negative region on the membrane instead of the anti-carrier antibodies. In another embodiment, an anti-target compound antibody optionally conjugated with biotin or other protein-binding molecules is used as a binding agent. In this case, the recombinant protein expressed by the recombinant spore comprises streptavidin/avidin, proteins specifically binding to the above protein-binding molecules, or protein A, protein G, protein L, protein A/G or other antibody binding proteins capable of binding to the constant region of the above anti-target compound antibody. The anti-target compound antibody may also be displayed on the surface of the spore as a fusion protein.

In one embodiment, a fluorescent protein is displayed on the surface of the spore. In a preferred embodiment, the fluorescent protein is displayed on the surface of the spore through recombinant techniques known in the art. In one embodiment, the fluorescent protein is enhanced green fluorescent protein (eGFP), green fluorescent protein (GFP), red fluorescent protein (RFP), or yellow fluorescent protein (YFP). In a preferred embodiment, the fluorescent protein is eGFP. In another embodiment, the fluorescence signal on the spore is detected by a fluorescence detector, such as a fluorescence microscope, without any AuNPs or other labels.

In one embodiment, the recombinant protein expressed by the recombinant spore includes eGFP (as a signal-producing substance) and a target-binding protein specifically binding to the target compound. The target compound and a carrier protein are linked to form carrier-target, which serves as a competing agent. Anti-carrier antibodies are immobilized in the negative region on the membrane, and anti-spore antibodies or antibodies against the target-binding protein are immobilized in the positive region on the membrane, wherein the negative region is closer to the sample introduction site on the membrane, and the positive region is closer to the absorption pad on the membrane. The sample, the above spore, and the carrier-target are then mixed so that competition can occur between the target compound contained in the sample and the competing agent for binding to the target-binding protein on the spore can. The presence or absence of GFP signal in the positive or negative region is then observed under fluorescence microscope. Alternatively, the above competing agent is immobilized in the negative region on the membrane instead of the anti-carrier antibodies. In another embodiment, an anti-target compound antibody optionally conjugated with biotin or other protein-binding molecules is used as a binding agent. In this case, the recombinant protein expressed by the recombinant spore comprises eGFP (as a signal-producing substance) and streptavidin/avidin, proteins specifically binding to the above protein-binding molecules, or protein A, protein G, protein L, protein A/G or other antibody binding proteins capable of binding to the constant region of the above anti-target compound antibody. The anti-target compound antibody may also be displayed on the surface of the spore as a fusion protein.

When the analyte is an antibody, the recombinant protein expressed by the recombinant spore comprises an antigen recognized by the target antibody. The above AuNP-Ab complex (as a signal-producing substance) and the spore are mixed to form an AuNP-Ab-spore complex. An antibody against the constant region of the target antibody is immobilized in the positive region on the membrane, and an anti-spore antibody (said antibody and the antibody conjugated with AuNP bind to different epitopes on the spore) or an antibody against the recombinant protein is immobilized in the negative region on the membrane, wherein the positive region is closer to the sample introduction site on the membrane, and the negative region is closer to the absorption pad on the membrane. The sample and the above AuNP-Ab-spore complex are then mixed for reaction to occur.

In one embodiment, the recombinant protein expressed by the recombinant spore comprises an antibody, protein A, protein G, protein L, protein A/G or other antibody binding proteins capable of binding to the constant region of the target antibody. The above AuNP-Ab complex (as a signal-producing substance) and the spore are mixed to form an AuNP-Ab-spore complex. An antigen recognized by the target antibody is immobilized in the positive region on the membrane, and an anti-spore antibody (said antibody and the antibody conjugated with AuNP bind to different epitopes on the spore) or an antibody against the recombinant protein is immobilized in the negative region on the membrane, wherein the positive region is closer to the sample introduction site on the membrane, and the negative region is closer to the absorption pad on the membrane. The sample and the above AuNP-Ab-spore complex are then mixed for reaction to occur. In another embodiment, an antibody capable of binding to the constant region of the target antibody optionally conjugated with biotin or other protein-binding molecules may be used as a binding agent. In this case, the recombinant protein is streptavidin/avidin, a protein specifically binding to the above protein-binding molecules, or protein A, protein G, protein L, protein A/G or other antibody binding proteins capable of binding to the constant region of the above binding agent.

In one embodiment, a fluorescent protein is displayed on the surface of the spore. In a preferred embodiment, the fluorescent protein is displayed on the surface of the spore through recombinant techniques known in the art. In one embodiment, the fluorescent protein is enhanced green fluorescent protein (eGFP), green fluorescent protein (GFP), red fluorescent protein (RFP), yellow fluorescent protein (YFP). In a preferred embodiment, the fluorescent protein is eGFP. In another embodiment, the fluorescence signal on the spore is detected by a fluorescence detector, such as a fluorescence microscope in the absence of any AuNPs or other labels.

In one embodiment, the recombinant protein expressed by the recombinant spore includes eGFP (as a signal-producing substance) and an antigen recognized by the target antibody. An antibody against the constant region of the target antibody is immobilized in the positive region on the membrane, and an anti-spore antibody or an antibody against the recombinant protein is immobilized in the negative region on the membrane, wherein the positive region is closer to the sample introduction site on the membrane, and the negative region is closer to the absorption pad on the membrane. The sample and the above spore are then mixed for reaction to occur. In another embodiment, the recombinant protein expressed by the recombinant spore includes eGFP (as a signal-producing substance) and an antibody, protein A, protein G, protein L, protein A/G or other antibody binding proteins capable of binding to the constant region of the target antibody. An antigen recognized by the target antibody is immobilized in the positive region on the membrane, and an anti-spore antibody or an antibody against the recombinant protein is immobilized in the negative region on the membrane, wherein the positive region is closer to the sample introduction site on the membrane, and the negative region is closer to the absorption pad on the membrane. The sample and the spore are then mixed for reaction to occur. In another embodiment, an antibody capable of binding to the constant region of the target antibody optionally conjugated with biotin or other protein-binding molecules is used as a binding agent. In this case, the recombinant protein includes eGFP (as a signal-producing substance) and streptavidin/avidin, a protein specifically binding to the above protein-binding molecules, or protein A, protein G, protein L, protein A/G or other antibody binding proteins capable of binding to the constant region of the above binding agent.

When the analyte is a protein, an anti-target protein antibody is optionally conjugated with biotin or other protein-binding molecules to serve as a binding agent. The recombinant protein expressed by the recombinant spore comprises streptavidin/avidin, a protein specifically binding to the above protein-binding molecules, or protein A, protein G, protein L, protein A/G or other antibody binding proteins capable of binding to the constant region of the above binding agent. The above binding agent binds to the spore to form a spore-Ab complex. Alternatively, the anti-target protein antibody is displayed on the surface of the spore as a fusion protein. The above AuNP-Ab complex (as a detecting agent) reacts with the spore-Ab complex to form an AuNP-Ab-spore-Ab complex. Another anti-target protein antibody is immobilized in the positive region on the membrane, and an antibody against the constant region in the spore-Ab complex is immobilized in the negative region on the membrane, wherein the positive region is closer to the sample introduction site on the membrane, and the negative region is closer to the absorption pad on the membrane. The sample and the above AuNP-Ab-spore-Ab complex are then mixed for reaction to occur. In one embodiment, a fluorescent protein is displayed on the surface of the spore. In a preferred embodiment, the fluorescent protein is displayed on the surface of the spore through recombinant techniques known in the art. In one embodiment, the fluorescent protein is enhanced green fluorescent protein (eGFP), green fluorescent protein (GFP), red fluorescent protein (RFP), yellow fluorescent protein (YFP). In a preferred embodiment, the fluorescent protein is eGFP. In another embodiment, the fluorescence signal on the spore is detected by a fluorescence detector, such as a fluorescence microscope in the absence of any AuNPs or other labels.

In one embodiment, an anti-target protein antibody is optionally conjugated with biotin or other protein-binding molecules to serve as a binding agent. The recombinant protein expressed by the recombinant spore includes eGFP (as a signal-producing substance) and streptavidin/avidin, a protein specifically binding to the above protein-binding molecules, or an antibody, protein A, protein G, protein L, protein A/G or other antibody binding proteins capable of binding to the constant region of the binding agent. The above binding agent binds to the spore to form a spore-Ab complex. Alternatively, the anti-target protein antibody is displayed on the surface of the spore as a fusion protein. Another anti-target protein antibody is immobilized in the positive region on the membrane, and an antibody against the constant region of the spore-Ab complex is immobilized in the negative region on the membrane, wherein the positive region is closer to the sample introduction site on the membrane, and the negative region is closer to the absorption pad on the membrane. The sample and the above spore-Ab complex are then mixed for reaction to occur.

Detection by ELISA

The detection system of the present invention can be used to detect the presence of an analyte in a sample through ELISA commonly use in the art. In one embodiment, the analyte is a compound and the target compound is linked to a carrier protein to form carrier-target, which serves as a competing agent. The recombinant protein expressed by the recombinant spore comprises a target binding protein specifically binding to the target compound. An anti-carrier protein antibody is immobilized on an ELISA plate. The sample, the competing agent and the spore are then mixed and introduced to the ELISA plate for competition between the target compound in the sample and the competing agent for binding to the target binding protein on the spore to occur. A signal-producing substance selected from the following is added to the plate for detection: an anti-spore antibody conjugated with an enzyme which converts a substrate providing no signal to a substrate providing a signal; an anti-spore antibody and an antibody against the constant region of the former antibody conjugated with an enzyme which converts a substrate providing no signal to a substrate providing a signal; and an anti-spore antibody and protein A, protein G, protein L, protein A/G or other antibody binding proteins capable of binding to the constant region of the former antibody conjugated with an enzyme which converts a substrate providing no signal to a substrate providing a signal. Alternatively, an enzyme which converts a substrate providing no signal to a substrate providing a signal is also displayed on the surface of the spore as a recombinant protein. The substrate of the above enzyme is then added to the plate for reaction to occur. In another embodiment, the carrier-target (i.e., the competing agent) is immobilized on the ELISA plate to compete with the target compound for binding to the target binding protein on the spore.

In a further embodiment, an anti-target compound antibody optionally conjugated with biotin or other protein-binding molecules is used as a binding agent. In this case, the recombinant protein expressed by the recombinant spore is streptavidin/avidin, a protein specifically binding to the above protein-binding molecules, or protein A, protein G, protein L, protein A/G or other antibody binding proteins capable of binding to the constant region of the above binding agent. Alternatively, the anti-target compound antibody is displayed on the surface of the spore as a fusion protein.

When the analyte is an antibody, the recombinant protein expressed by the recombinant spore comprises an antigen recognized by the target antibody. An antibody, protein A, protein G, protein L, or protein A/G or other antibody binding proteins capable of binding to the constant region of the target antibody are immobilized on an ELISA plate. The sample and the above spore are then mixed and introduced to the ELISA plate. A signal-producing substance mentioned above for detection of a compound by ELISA and the substrate of the enzyme concerned are also added to the plate for reaction to occur. In one embodiment, an antigen recognized by the target antibody is immobilized on an ELISA plate. The recombinant protein expressed by the recombinant spore is an antibody, protein A, protein G, protein L, protein A/G or other antibody binding proteins capable of binding to the constant region of the target antibody. The sample and the above spore are then mixed and introduced to the ELISA plate. A signal-producing substance mentioned above for detection of a compound by ELISA and the substrate of the enzyme concerned are also added to the plate for reaction to occur. In another embodiment, an antibody capable of binding to the constant region of the target antibody optionally conjugated with biotin or other protein-binding molecules is used as a binding agent. In this case, the recombinant protein expressed by the recombinant spore comprises streptavidin/avidin, a protein specifically binding to the above protein-binding molecule, or protein A, protein G, protein L, protein A/G or other antibody binding proteins capable of binding to the constant region of the above anti-target protein antibody.

When the analyte is a protein, an anti-target protein antibody optionally conjugated with biotin or other protein-binding molecules is used as a binding agent. The recombinant protein expressed by the recombinant spore comprises streptavidin/avidin, a protein specifically binding to the above protein-binding molecule, or an antibody, protein A, protein G, protein L, protein A/G or other antibody binding proteins capable of binding to the constant region of the above anti-target protein antibody. The above anti-target protein antibody then binds to the spore to form a spore-Ab complex. Alternatively, the anti-target protein antibody is displayed on the surface of the spore in the form of a fusion protein. Another anti-target protein antibody is immobilized on an ELISA plate, to which the sample and the above spore-Ab complex are introduced. A signal-producing substance mentioned above for detection of a compound by ELISA and the substrate of the enzyme concerned are also added to the plate for reaction to occur.

Further details of the invention are illustrated by the following non-limiting examples.

Example 1: Surface Display of Fusion Proteins 1-1 Plasmid Construction

The recombinant plasmids for use in the present invention were produced through conventional recombinant techniques known in the art.

pSH-SA

CotB (Kunst et. al., 1997) and streptavidin (SA) genes were cloned into shuttle vector pMK4 (BCRC 41416, purchased from Bioresource Collection and Research Center (BCRC), Taiwan) with replication origin ori and cleavage sites for restriction enzyme HindIII, PstI, BamHI, EcoRI, NdeI and SpeI and selectable markers including Ampicillin resistance gene (AmpR(bla)) and Chloramphenicol acetyltransferase (CmR(cat)) to form recombinant plasmid pSH-SA through use of *Escherichia coli* DH5α (obtained from Dr. Chih-Hung Huang at National Taipei University of Technology, Taiwan) with genotype thuA2 lacΔU169 phoA glnV44Φ80' lacZΔM15 gyrA96 recA1 relA1 endA1thi-1 hsdR17 (Taylor et al., 1993). The cotB DNA fragment containing the promoter and structure gene without stop codon of cotB, cgtcgtcgtcgtcgtcgatcg (SEQ ID NO: 6) DNA sequence and cotB terminator was synthesized by Protech (Taipei, Taiwan). The synthetic DNA also contains restriction-enzyme cutting sites including PstI, SalI, and XhoI at the cotB promoter end and NheI, and EcoRI at the other end. This DNA fragment was inserted between PstI and EcoRI sites of pMK4 (Sullivan, et al., 1984). The resulting plasmid is called pWL-cotB. Another DNA fragment containing cgatcgcgtcgtcgtcgtcgtcgtcgtcgtcgt (SEQ ID NO: 7) DNA sequence and the gene for amino acid 13 to 140 of streptavidin, the biotin-binding site (Argarana, et al., 1986), was also synthesized by Protech (Taipei, Taiwan). This DNA fragment also contains the terminator of cotB gene and restriction-enzyme cutting sites including BamHI, and EcoRI at the cotB terminator end and NheI at the other end. The DNA fragment was inserted between NheI and EcoRI sites of pWL-cotB. The new plasmid is named pSH-SA. The plasmid map of pSH-SA is shown in FIG. 1.

pSH-SA-eGFP

The cotC (Negri et al., 2013) and eGFP (Ning et al., 2011) genes were cloned into pSH-SA. The cotC-eGFP DNA fragment was synthesized by Protech (Taipei, Taiwan). It contains the promoter and structure gene without stop codon of cotC, the structure gene with stop codon of eGFP and cotC terminator (SEQ ID NO:2). This DNA fragment also contains restriction-enzyme cutting sites including PstI at the cotC promoter end and XhoI at the cotC terminator end. The DNA fragment was inserted between PstI and XhoI sites of pSH-SA. The new plasmid is named pSH-SA-eGFP.

pH-SA-eGFP

Figure 2:
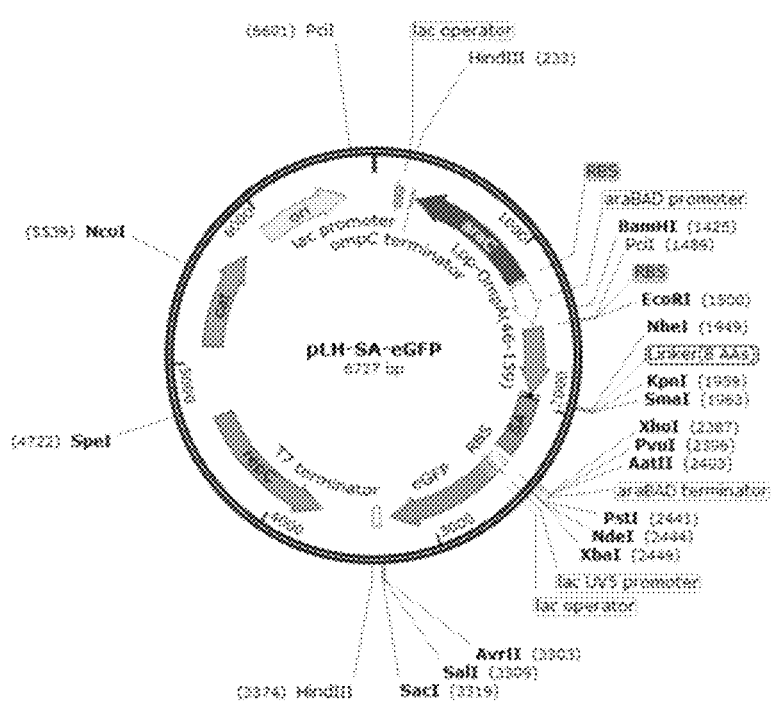
FIG. 2 shows the plasmid map of pLH-SA-eGFP.

DNA fragment $P_{araBAD}$-Lpp-OmpA(46-159)-SA-$P_{lacUV5}$-eGFP (HindIII-ompC terminator-araC-$P_{araBAD}$-Lpp-OmpA (46-159)-(L8)-SA-$P_{lacUV5}$-eGFP-T7 terminator-HindIII) of 3147 bp with the nucleotide sequence shown in SEQ ID NO: 3 was first synthesized and cloned into pMK4 (between HindIII and HindIII) so as to obtain a plasmid named pLH-SA-eGFP. The plasmid map of pLH-SA-eGFP is shown in FIG. 2.

Figure 3:
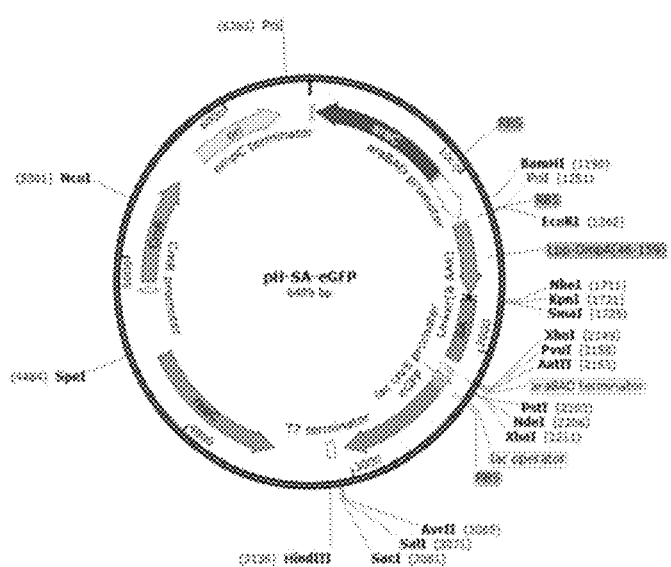
FIG. 3 shows the plasmid map of pH-SA-eGFP.

Use pLH-SA-eGFP as a template for PCR with primers del-F (CAATGAAAAAAGGGCCCGCA; SEQ ID NO: 4) and del-R (TCTTCCGCTTCCTCGCTCA; SEQ ID NO: 5) to remove the sequence between nucleotides 1 and 238 to obtain a plasmid named pH-SA-eGFP. The plasmid map of pH-SA-eGFP is shown in FIG. 3.

1-2 Preparation of Competent Cells

B. Subtilis

B. subtilis 168 with genotype trpC2 (BCRC 17890; purchased from Bioresource Collection and Research Center (BCRC), Taiwan) (Zeigler et al., 2008) was chosen for use in the present invention. Before transformation of the plasmid, the bacterial culture of B. subtilis 168 cultured overnight at 37° C. was added to a flask containing LBS medium (LB broth (containing 2.5 g of yeast extract (BIONOVAS; catalog no. 8013-01-2), 5 g of tryptone (PROADISA; catalog no. 1612.00), 5 g of NaCl (AMRESCO; catalog no. 241-1KG) and 500 mL of reverse osmosis (RO) water) with 0.5 M sorbitol (ACROS; catalog no. 132735000)). The starting concentration of the bacterial culture was diluted around 100-fold ($OD_{600}$≈0.05) (measured by the spectrophotometer purchased from TiHalinko Technology CO., Ltd., Taiwan), followed by subculturing the same at a 37° C. water bath. When the $OD_{600}$ value was about 0.85 (no more than 1), the bacterial culture was placed on ice for 10 minutes. The bacterial culture was then placed in a 50 mL conical tube, centrifuged under 5000×g for 10 minutes at 4° C., followed by disposal of the supernatant. Afterward, MSG buffer (comprising 0.5M mannitol (ACROS; catalog no. 125345000), 0.5M sorbitol (ACROS; catalog no. 132735000) and 10% v/v glycerol (J. T. Baker; catalog no. 2136-01)) with the same volume as the original culture was added to resuspend the precipitate, followed by centrifugation under 5000×g for 10 minutes at 4° C. and disposal of the supernatant. The above step was repeated three times, and MSG buffer with the volume 1/80 of the original culture volume was added to resuspend the cells, followed by distributing the same in microcentrifuge tubes (around 60 µl in each tube) for storage at −80° C.

E. Coli

DH5α was used as a competent cell. The bacteria were cultured overnight at 37° C. and added to a conical flask containing liquid culture medium; the initial concentration of the bacterial culture was diluted to 1/100 and placed in a 37° C. water bath for about 2 hours. When OD600 reaches 0.4 (no greater than 0.8), the culture was placed on ice for 10 minutes. The bacterial culture was then placed in a 50 mL conical tube, centrifuged under 1000×g for 15 minutes at 4° C., followed by disposal of the supernatant. Afterward, ice cold sterilized water was added so as to gently resuspend the precipitate, followed by centrifugation under 1000×g for 20 minutes at 4° C. and disposal of the supernatant. Ice cold 10% v/v glycerol with the same volume as the original culture was added to resuspend the precipitate, followed by centrifugation under 1000×g for 20 minutes at 4° C.; the supernatant was carefully removed so as to avoid removing the cells. All of the precipitates were resuspended in a suitable amount $$\left(\text{the volume of the subculture} \times \frac{OD_{600}}{50\sim60}\right)$$

of 10% glycerol and distributed in microcentrifuge tubes (40 µl in each tube) for storage at −80° C.

1-3 Transformation

B. Subtilis

The plasmid constructed above was delivered to B. subtilis 168 through electroporation with selection based on antibiotic genes. Said process comprises the following steps: dissolving the competent cells originally stored at −80° C. and adding a suitable amount of plasmid (about 1 to 2 µl) followed by gently tapping the tube for mixture and placing the mixture in ice for 1 minute; placing the mixture in a electroporation cuvette (BTX Cuvette; Level Biotechnology Inc., Taiwan) pre-cooled at −20° C., drying the outer part of the cuvette with kimwipes followed by placement of the same in the electroporation cuvette (1 mm gap) of the electroporation instrument (CellJect Duo, Termo Hybrid and BTX ECM 399, Level Biotechnology Inc.) and pulse activation for electric shock (voltage: 2000 volts; capacitance: 15 µf; shunt resistance: 335R); taking out the cuvette immediately after completion of the electric shock, adding 1 ml of LB medium to the cuvette to be mixed, followed by taking out the bacterial culture from the cuvette, placing the same in microtubes, and culturing the same at 37° C. for 3 hours; centrifuging the bacterial culture under 12000×g for 3 minutes, disposing the supernatant so that the residual volume is around 100 µl, well mixing the bacterial culture and evenly plating the culture onto LB plate (with the same components as those of LB broth but with the addition of agarose) comprising antibiotics for selection, followed by a 16-hour culture; and selecting the growing colony and culturing the same for 16 to 18 hours for sporulation.

E. Coli

The plasmid constructed above was delivered to E. coli through electroporation with selection based on antibiotic genes. Said process comprises the following steps: dissolving the competent cells originally stored at −80° C. and adding a suitable amount of plasmid (about 1 to 2 µl) followed by gently tapping the tube for mixture and placing the mixture in ice for 1 minute; placing the mixture in a electroporation cuvette pre-cooled at −20° C., drying the outer part of the cuvette with kimwipes followed by placement of the same in the electroporation cuvette (1 mm gap) of the electroporation instrument and pulse activation for electric shock (voltage: 2000 volts; capacitance: 15 µF; shunt resistance: 335R); taking out the cuvette immediately after completion of the electric shock, adding 1 ml of 37° C. LB medium to the cuvette to be mixed, followed by taking out the bacterial culture from the cuvette, placing the same in microcentrifuge tubes, and culturing the same at 37° C. for 1 hour; centrifuging the bacterial culture under 12000×g for 3 minutes, disposing the supernatant so that the residual volume is around 100 µl, well mixing the bacterial culture and evenly plating the culture onto solid LB medium comprising antibiotics for selection, followed by a 16-hour culture.

1-4 Sporulation

Colonies of *B. subtilis* (B.s.168, B.s.168/pSH-SA or B.s.168/pSH-SA-eGFP) were inoculated in test tubes with addition of 5 ml of LB medium (containing 10 µl of Chloramphenicol at the concentration of 3 mg/ml) and cultured for 16 to 18 hours. 125 µl of cultured bacterial broth was placed in a flask with addition of 25 ml 2×SG medium and placed in 37° C. water bath for a culture (with a shaking speed of 200 rpm) for 48 hours. The cultured bacterial broth was then placed in a 50 ml conical tube and centrifuged under 10,000×g for 20 minutes at 4° C. Afterward, the precipitated spores were washed twice with PBS to remove residual nutrients and stored at 4° C. for future use.

After transformation, the transformed colony of *B. subtilis* was inoculated in 5 mL of LB broth (comprising selectable antibiotic marker) for a culture of 16 to 18 hours, followed by a sporulation method including the following steps (design based on "Molecular Biological Methods for *Bacillus*," edited by Colin R. Harwood & Simon M. Cutting; Chichester; John Wiley & Sons, 1990): diluting the bacterial culture 200 fold (125 µl, 25 ml) with 2×SG medium (comprising 16 g of Difco Nutrient broth (BD; catalog no. 234000 500G), 2 g of KCl (SIGMA; catalog no. 7447-40-7), 0.5 g of $MgSO_4$-$7H_2O$ (SIGMA; catalog no. .M1880-500G) and 1 L of RO water with addition of the following substances after sterilizing the mixture of the above with high temperature followed by cooling: 1 mL of 1 M $Ca(NO)_2$ (SIGMA; catalog no. C2786-500G), 1 mL of 0.1 M $MnCl_2$—$H_2O$ (SIGMA; catalog no. M1787-10X1ML), 1 mL of 1 mM FeSO4 (SIGMA; catalog no. 38047-1EA), and 2 mL of Glucose 50% (w/v), filtered sterilized) in a flask and placing the same in 37° C. water bath (with a shaking speed of 200 rpm) for culturing; observing the bacterial culture daily with optical microscopy with CCD (40×) (Olympus) for sporulation (more than 90% of the bacteria form spores after 3 days); placing the bacterial culture in a 50 mL conical tube and centrifuging the same at 10,000×g for 20 minutes at 4° C.; washing the spores with ice cold water to remove the residual nutrients and lyse the residual cells; and storing the spores at 4° C. and changing water every week, or placing the spores at −20° C. for long-term storage.

1-5 Growth of *E. Coli*

Transformed MG1655/pH-SA-eGFP colonies were inoculated in 5 ml of LB medium (containing 10 µl of Chloramphenicol at the concentration of 3 mg/ml) and cultured for 16 to 18 hours; the cultured bacterial broth was measured for $OD_{600}$. A suitable amount of bacterial culture was added to 25 ml of LB medium (containing 50 µl of Chloramphenicol at the concentration of 3 mg/ml), followed by an adjustment so that the $OD_{600}$ was 0.05 and a culture step performed in 37° C. water bath (with a shaking speed of 200 rpm). When $OD_{600}$ was 0.1, 2.5 µl of arabinose at the concentration of 0.1 M was added so that the final concentration was 10 µM; when $OD_{600}$ was 1, 25 µl of IPTG at the concentration of 100 mM was added so that the final concentration was 100 µM, followed by a culture step performed in 37° C. water bath (with a shaking speed of 200 rpm) for 16 to 18 hours. The bacterial culture was then centrifuged under 1000×g for 15 minutes, washed twice with PBS, and stored at 4° C. The above PBS contains 8 g NaCl, 0.2 g KCl, 1.44 g $Na_2HPO_4$, 0.24 g $KH_2PO_4$ and 1000 mL $H_2O$, with the pH adjusted to 7.4 with 1 M HCl.

Example 2: Detection of Anti-Streptavidin Antibody by LFA Using Spores and Gold Nanoparticles (AuNP)

2-1 Pretreatment of Spores

To 1000 µl of spores (B.s. 168/pH-SA-eGFP) with $OD_{600}$ of 1 was added 250 µl of 0.05% SDS and mixed for 30 minutes. The mixture was centrifuged twice (under 12000×g for 3 minutes), followed by addition of 1000 µl 1% BSA (w/v, BSA/PBS) and a mixing step for 2 hours. The spores were then centrifuged and mixed with 100 µl PBS so that the $OD_{600}$ was adjusted to about 10.

2-2 AuNP Modification

100 µl of potassium carbonate solution at the concentration of 26 mM was added to 600 µl of AuNP solution (0.355 nM) (final concentration: AuNP solution at 0.3 nM; potassium carbonate solution at 3.714 mM). 1 µl of anti-spore antibody (Mybiosource/mbs612878) at the concentration of 2 mg/ml was added and the mixture was stored at 4° C. for 16 hours, followed by addition of 200 µl of 5% BSA and waiting for 30 minutes. The mixture was then centrifuged under 4000×g at 4° C. for 40 minutes. Afterward, the supernatant was removed, and the precipitate was resuspended with 600 µl of PBS; the solution was stored at 4° C. for use.

2-3 Strip Preparation 2 mg/ml of anti-mouse IgG secondary antibody (SIGMA/M8890) and 1 mg/ml of anti-eGFP antibody (abcam/ab184601) were respectively dispensed to the positive line and the negative line on the membrane (Millipore/HF1200) (2 µl per cm on the membrane), followed by a drying step at room temperature for 2 hours. The membrane was then immersed in 1% PVA (polyvinyl alcohol) solution for 30 minutes followed by a drying step at room temperature for 2 hours. Afterward, the membrane was immersed in 5% sucrose solution for 30 seconds. After being dried, the membrane was cut into strips with a width of 0.5 cm and stored at 4° C.

2-4 Detection

100 µl of the pretreated spores was mixed with 100 µl of the modified AuNP for 30 minutes. The spores were then mixed thoroughly with 1 µl of the anti-streptavidin antibodies (abcam/ab10020) from mouse at different concentrations. Afterward, the strip was immediately placed in the above solution mixture, and a photograph was taken to record the result after drying for about 10 minutes.

2-5 Result

Figure 4:
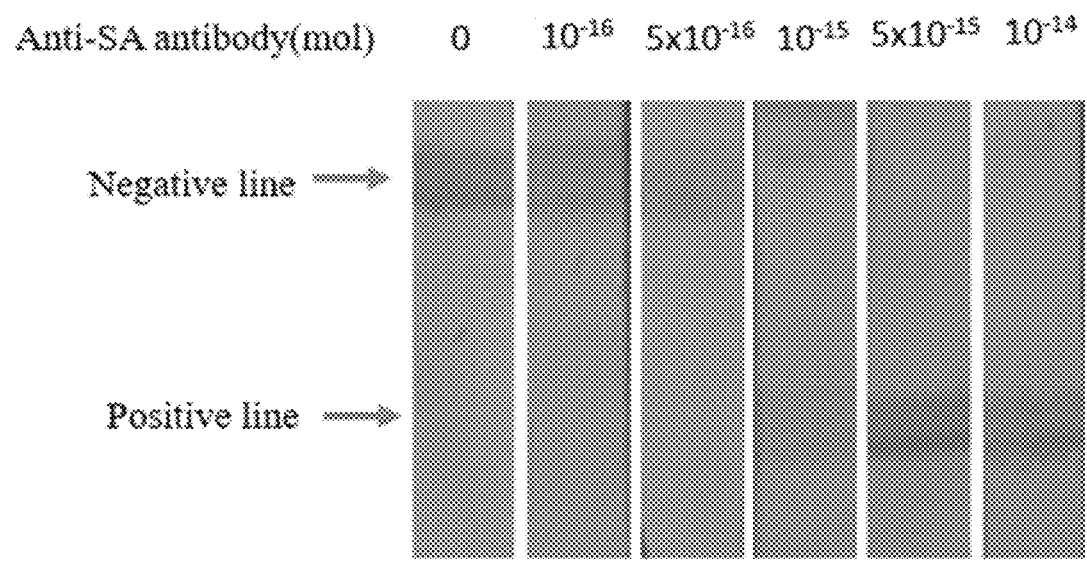
FIG. 4 shows the results of detection of anti-streptavidin antibody by LFA using spores and gold nanoparticles.

It was found that when the amount of the anti-streptavidin antibody is $10^{-15}$ mol, the positive line shows a signal, and the greater the antibody amount is, the stronger the signal is. On the other hand, at the negative line, the greater the antibody amount is, the weaker the signal is (see FIG. 4).

Example 3: Detection of β-galactosidase by LFA Using Spores and Gold Nanoparticles (AuNP)

3-1 Pretreatment of Spores

To 1000 µl of spores (B.s. 168/pSH-SA-eGFP) with $OD_{600}$ of 1 was added 250 µl of 0.05% SDS and mixed for 30 minutes. The mixture was centrifuged twice (under 12000×g for 3 minutes), followed by addition of 1000 µl 1% BSA (w/v, BSA/PBS) and a mixing step of 2 hours. The spores were then centrifuged and mixed with 100 µl PBS and the $OD_{600}$ was adjusted to about 10. Afterward, 100 µl of a biotinylated anti-β-gal antibody (abcam/ab6645) at the concentration of $10^{-7}$ M was added and mixed for 2 hours, followed by centrifuging the spores and adding 100 µl of PBS so that the $OD_{600}$ was adjusted to about 10.

3-2 AuNP Modification

100 µl of potassium carbonate solution at the concentration of 26 mM was added to 600 µl of AuNP solution (0.355 nM) (final concentration: AuNP solution at 0.3 nM; potassium carbonate solution at 3.714 mM). 1 µl of anti-spore antibody (Mybiosource/mbs612878) (from rabbit) at the concentration of 2 mg/ml was added and the mixture was placed at 4° C. for 16 hours, followed by addition of 200 µl of 5% BSA and waiting for 30 minutes. The mixture was then centrifuged under 4000×g at 4° C. for 40 minutes. Afterward, the supernatant was removed, and the precipitate was resuspended with 600 µl of PBS; the solution was stored at 4° C. for use.

3-3 Strip Preparation 1 mg/ml of anti-β-galactosidase antibody (Novusbio/NBP2-52702) and 2 mg/mL of goat anti-rabbit IgG antibody (abcam/ab6702) were respectively dispensed to the positive line and the negative line on the membrane (Millipore/HF1200) (2 µl per cm on the membrane), followed by a drying step at room temperature for 2 hours. The membrane was then immersed in 1% PVA for 30 minutes followed by a drying step at room temperature for 2 hours. Afterward, the membrane was immersed in 5% sucrose solution for 30 seconds. After being dried, the membrane was cut into strips with a width of 0.5 cm and stored at 4° C.

3-4 Detection

100 µl of the pretreated spores was mixed with 100 µl of the modified AuNP for 30 minutes. The spores were then mixed thoroughly with 1 µl of β-galactosidase at different concentrations. Afterward, the strip was immediately placed in the above solution mixture, and a photograph was taken to record the result after drying for about 10 minutes.

3-5 Result

Figure 5:
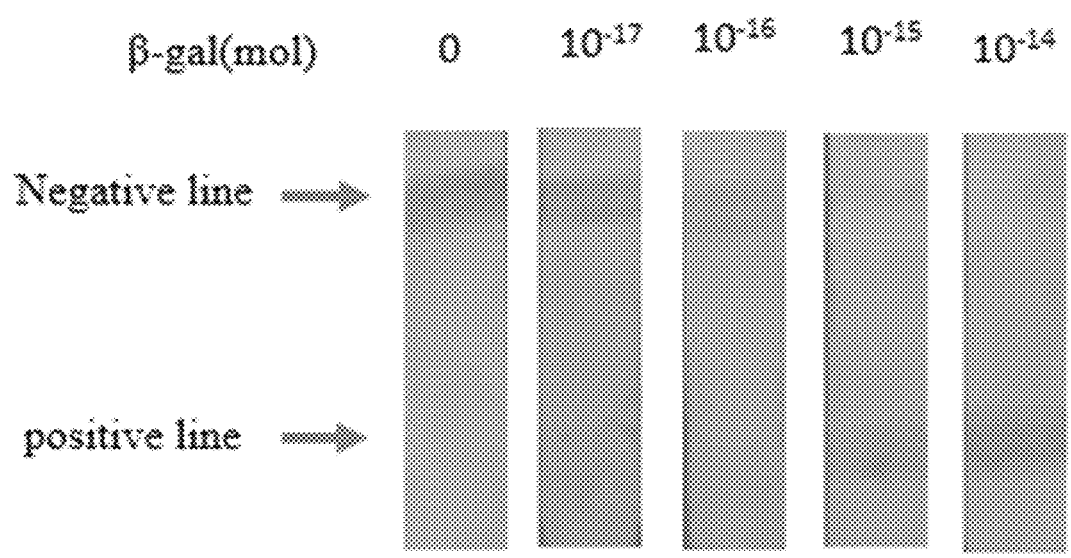
FIG. 5 shows the results of detection of β-galactosidase by LFA using spores and gold nanoparticles.

It was found that when the amount of β-galactosidase is $10^{-15}$ mol, the positive line shows a signal, and the larger the β-galactosidase amount is, the stronger the signal is. On the other hand, at the negative line, the greater the β-galactosidase amount is, the weaker the signal is (see FIG. 5).

Example 4: Detection of Biotin by LFA Using Spores and Gold Nanoparticles (AuNP)

4-1 Pretreatment of Spores

To 1000 µl of spores (B.s. 168/pH-SA-eGFP) with $OD_{600}$ of 1 was added 250 µl of 0.05% SDS and mixed for 30 minutes. The mixture was centrifuged twice (under 12000×g for 3 minutes), followed by addition of 1000 µl 1% PVA and a mixing step of 2 hours. The spores were then centrifuged and mixed with 100 µl PBS and the $OD_{600}$ was adjusted to about 10.

4-2 AuNP Modification

100 µl of potassium carbonate solution at the concentration of 26 mM was added to 600 µl of AuNP solution (0.355 nM) (final concentration: AuNP solution at 0.3 nM; potassium carbonate solution at 3.714 mM). 1 µl of anti-spore antibody (Mybiosource/mbs612878) at the concentration of 2 mg/ml was added and the mixture was placed at 4° C. for 16 hours, followed by addition of 200 µl of 5% BSA and waiting for 30 minutes. The mixture was then centrifuged under 4000×g at 4° C. for 40 minutes. Afterward, the supernatant was removed, and the precipitate was resuspended with 600 µl of PBS; the solution was stored at 4° C. for use.

4-3 Strip Preparation 1 mg/ml of anti-eGFP antibody (abcam/ab184601) and 2 mg/ml of anti-BSA antibody (SIGMA/B2901) were respectively dispensed to the positive line and the negative line on the membrane (Millipore/HF1200) (2 µl per cm on the membrane), followed by a drying step at room temperature for 2 hours. The membrane was then immersed in 1% PVA for 30 minutes followed by a drying step at room temperature for 2 hours. Afterward, the membrane was immersed in 5% sucrose solution for 30 seconds. After being dried, the membrane was cut into strips with a width of 0.5 cm and stored at 4° C.

4-4 Detection

100 µl of the pretreated spores was mixed with 1 µl of biotin at different concentrations for 2 hours, followed by addition of 100 µl of $10^{-7}$ M biotin-BSA for a mixing step of 30 minutes. The mixture was then centrifuged to remove the supernatant, and the precipitate was resuspended with 100 µl PBS. Afterward, the strip was placed in the above solution mixture. After being dried, AuNP wherein the surface thereof is modified with an anti-spore antibody was added. A photograph was taken to record the result after drying for about 10 minutes.

4-5 Result

Figure 6:
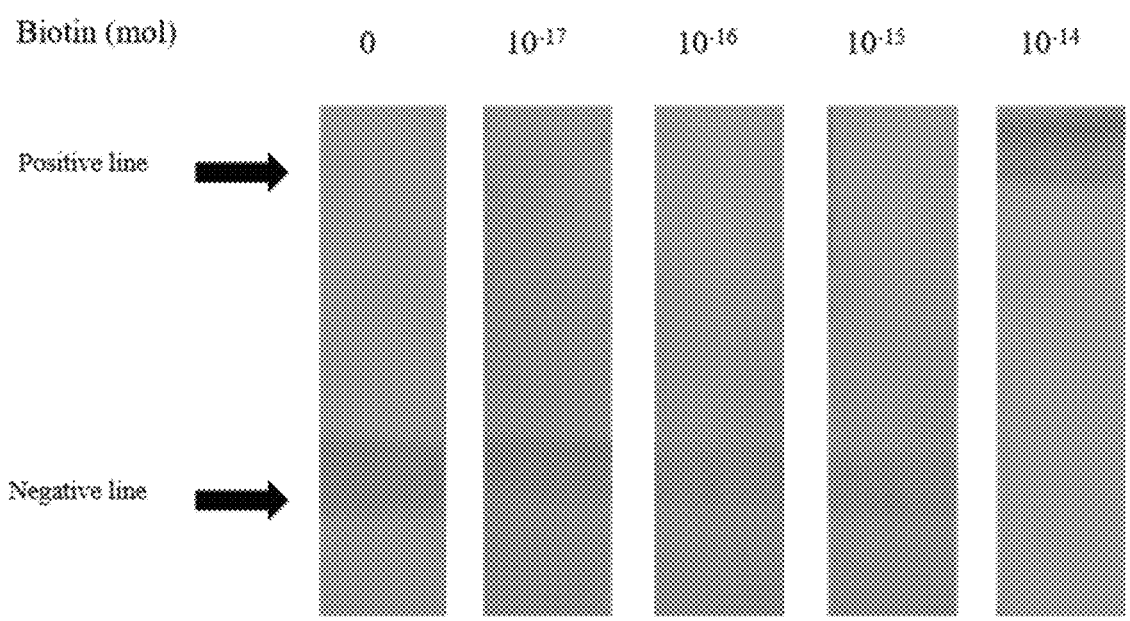
FIG. 6 shows the results of detection of biotin by LFA using spores and gold nanoparticles.

It was found that when the amount of biotin is $10^{-15}$ mol, the positive line shows a faint signal, and the greater the biotin amount is, the stronger the signal is. On the other hand, at the negative line, the greater the biotin amount is, the weaker the signal is (see FIG. 6).

Example 5: Detection of Anti-Streptavidin Antibody by LFA Using Spores and Fluorescence (eGFP)

5-1 Pretreatment of Spores

To 1000 µl of spores (B.s. 168/pSH-SA-eGFP) with $OD_{600}$ of 1 (about $5 \times 10^7$ spores/mL) was added 250 µl of 0.05% SDS and mixed for 30 minutes. The mixture was centrifuged twice (under 12000×g for 3 minutes), followed by addition of 1000 µl 1% BSA (w/v, BSA/PBS) and a mixing step of 2 hours. The spores were then centrifuged and mixed with 100 µl PBS so that the $OD_{600}$ was adjusted to about 10.

5-2 Strip Preparation 2 mg/ml of anti-mouse IgG secondary antibody (SIGMA/M8890) and 1 mg/ml of anti-eGFP antibody (abcam/ab184601) were respectively dispensed to the positive line and the negative line on the membrane (Millipore/HF1200) (2 µl per cm on the membrane), followed by a drying step at room temperature for 2 hours. The membrane was then immersed in 1% PVA for 30 minutes followed by a drying step at room temperature for 2 hours. Afterward, the membrane was immersed in 5% sucrose solution for 30 seconds. After being dried, the membrane was cut into strips with a width of 0.5 cm and stored at 4° C.

5-3 Detection

100 µl of the pretreated spores was mixed thoroughly with 1 µl of the anti-streptavidin antibody at different concentrations. Afterward, the strip was immediately placed in the above solution mixture, dried for about 10 minutes, and observed with an inverted fluorescence microscope (Leica DMi8); the magnification was set to be 2.5× using software MetaMorph, and the contrast was adjusted followed by recording through photographs.

5-4 Result

It was found that when the amount of the anti-streptavidin antibody is $10^{-17}$ mol, the positive line shows a signal, and the greater the antibody amount is, the stronger the signal is.

Figure 7:
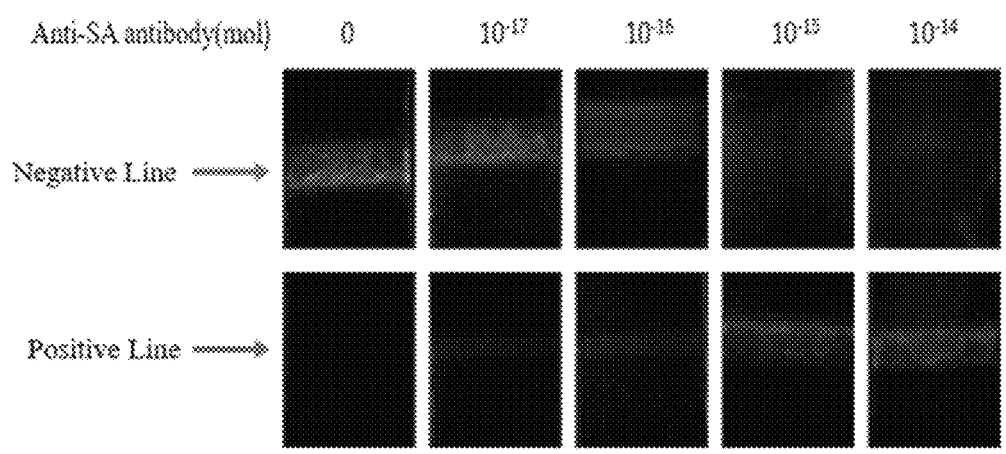
FIG. 7 shows the results of detection of anti-streptavidin antibody by LFA using spores and fluorescence (eGFP).

On the other hand, at the negative line, the greater the antibody amount is, the weaker the signal is (see FIG. 7).

Example 6: Detection of Anti-Streptavidin Antibody by LFA Using *E. Coli* and Gold Nanoparticles (AuNP)

6-1 AuNP Modification

100 μl of potassium carbonate solution at the concentration of 26 mM was added to 600 μl of AuNP solution (0.355 nM) (final concentration: AuNP solution at 0.3 nM; potassium carbonate solution at 3.714 mM). 1 μl of anti-*E. coli* antibody (abcam/ab137967) (from rabbit) at the concentration of 5 mg/ml was added and the mixture was placed at 4° C. for 16 hours, followed by addition of 200 μl of 5% BSA and waiting for 30 minutes. The mixture was then centrifuged under 4000×g at 4° C. for 40 minutes. Afterward, the supernatant was removed, and the precipitate was resuspended with 600 μl of PBS; the solution was stored at 4° C. for use.

6-2 Membrane Preparation

1 μL of 2 mg/ml of anti-mouse IgG secondary antibody (SIGMA/M8890) and 1 μL of 2 mg/ml of anti-streptavidin antibody (abcam/ab10020) were respectively dropped to the positive dot and the negative dot on the membrane (Millipore/HF1200), followed by a drying step at room temperature for 2 hours. The membrane was then immersed in 1% PVA for 30 minutes followed by a drying step at room temperature for 2 hours. Afterward, the membrane was immersed in 5% sucrose solution for 30 seconds. After being dried, the membrane was stored at 4° C.

6-3 Detection

100 μl of the cultured *E. coli* (MG1655/pH-SA-eGFP) was mixed with 100 μl of the modified AuNP for 30 minutes. The cells were then mixed thoroughly with 1 μl of the test antibody (abcam/ab10020) from mouse at different concentrations. Afterward, the membrane was immediately placed in the above solution mixture, and a photograph was taken to record the result after drying for about 10 minutes.

6-4 Result

Figure 8:
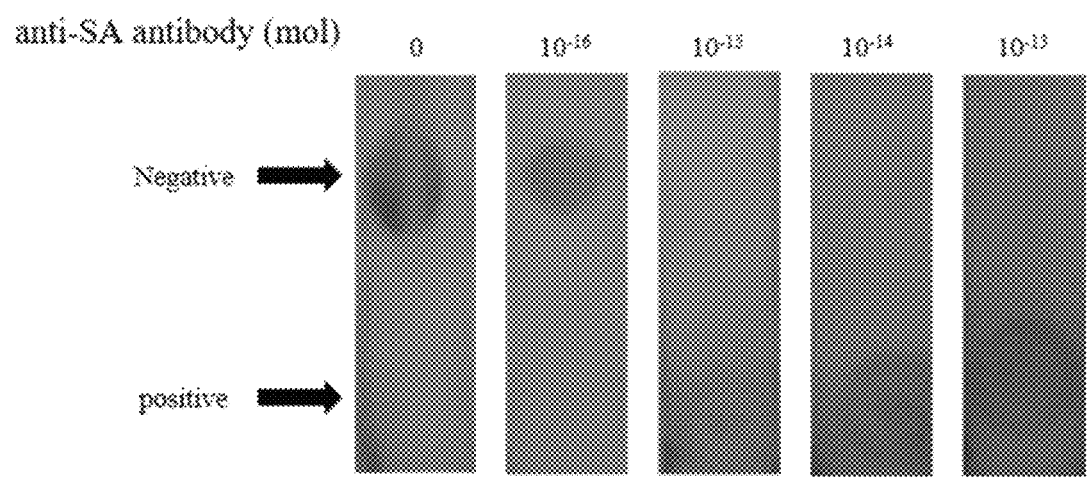
FIG. 8 shows the results of detection of anti-streptavidin antibody by LFA using E. coli and gold nanoparticles.

It was found that when the amount of the anti-streptavidin antibody is $10^{-15}$ mol, the positive line shows a signal, and the greater the antibody amount is, the stronger the signal is. On the other hand, at the negative line, the greater the antibody amount is, the weaker the signal is (see FIG. 8).

Example 7: Detection of Anti-Streptavidin Antibody by LFA Using *E. Coli* and Fluorescence (eGFP)

7-1 Membrane Preparation

1 μL of 2 mg/ml of anti-mouse IgG secondary antibody (SIGMA/M8890) and 2 mg/ml of anti-streptavidin antibody (abcam/ab10020) were respectively dropped to the positive dot and the negative dot on the membrane (Millipore/HF1200), followed by a drying step at room temperature for 2 hours. The membrane was then immersed in 1% PVA for 30 minutes followed by a drying step at room temperature for 2 hours. Afterward, the membrane was immersed in 5% sucrose solution for 30 seconds. After being dried, the membrane was stored at 4° C.

7-2 Detection

100 μl of the cultured *E. coli* (MG1655/pH-SA-eGFP) was mixed thoroughly with 1 μl of test antibody (abcam/ab10020) from mouse at different concentration. Afterward, the membrane was immediately placed in the above solution mixture, dried for about 10 minutes, and observed with an inverted fluorescence microscope (Leica DMi8); the magnification was set to be 2.5× using software MetaMorph, and the contrast was adjusted followed by recording through photographs.

7-3 Result

Figure 9:
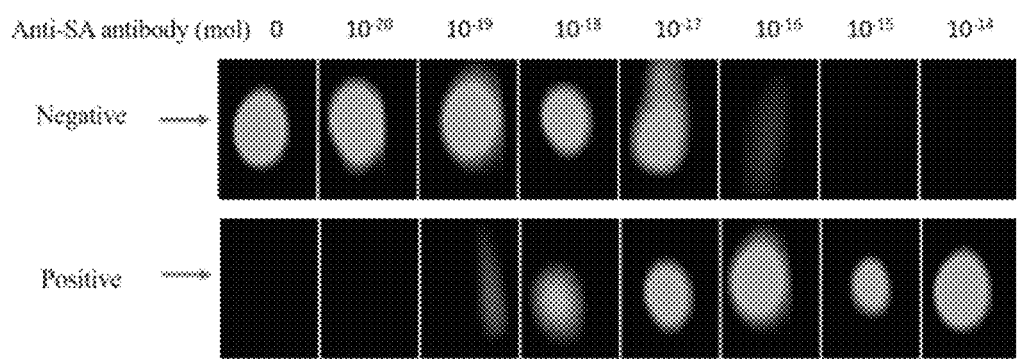
FIG. 9 shows the results of detection of anti-streptavidin antibody by LFA using E. coli and fluorescence (eGFP).

It was found that when the amount of the antibody is $10^{-19}$ mol, the positive line showed a signal; when the amount was between $10^{-19}$ mol and $10^{-17}$ mol, the greater the antibody amount is, the stronger the signal; when the concentration was between $10^{-17}$ mol and $10^{-14}$ mol, the signals did not significant vary since they were all very strong. At the negative line, when the amount was between $10^{-20}$ mol and $10^{-17}$ mol, the signals did not significant vary since they were all very strong; when the amount was $10^{-16}$ mol, the signal weakened; and when the amount was between $10^{-15}$ mol and $10^{-14}$ mol, there was no signal (see FIG. 9).

Example 8: Detection of Anti-Streptavidin Antibody by ELISA Using Spores and HRP/3,3',5,5'-Tetramethylbenzidine (TMB)

8-1 Preparation of ELISA Plate

The ELISA plate (GeneDireX/2115-196J) was washed 3 times with 200 μl of PBS/T (PBS with 0.05% Tween 20), followed by addition of 1 μl of a goat-anti-mouse IgG antibody (SIGMA/M8890) at the concentration of 2 mg/ml and 100 μl of coating buffer (1.89 g $NaHCO_3$ and 0.954 g $Na_2CO_3$ in 500 mL $H_2O$). After being placed at 4° C. for 18 hours, the plate was washed 3 times with 200 μl of PBS/T, followed by addition of 200 μl of 5% skim milk. After 90 minutes, the plate was washed 3 times with 200 μl of PBS/T.

8-2 ELISA

1000 μl of spores (B.s. 168/pSH-SA) with $OD_{600}$ of 1 was centrifuged under 12000×g for 3 minutes, followed by removing the supernatant and adding 80 μl of PBS and 10 μl of anti-streptavidin antibody (abcam/ab10020) at different concentrations and mixing with 10 μl of an anti-spore antibody (mybiosource/mbs612878) at the concentration of $10^{-8}$ M for 2 hours. The mixture was then centrifuged under 12000×g for 3 minutes, followed by removing the supernatant and adding 100 μl of PBS. The solution was added to the ELISA plate as prepared above for a mixing step of 2 hours. Afterward, the plate was washed 3 times with 200 μl of PBS/T; to the plate was then added 100 μl of goat-anti-rabbit IgG (HRP) (abcam/ab6721) at the concentration of 0.2 μg/ml for a mixing time of 30 minutes, followed by washing 10 times with 200 μl of PBS/T (each time includes an immersing step of 2 minutes). 100 μl of 3,3',5,5'-Tetramethylbenzidine (TMB Substrate, Thermo Scientific/34021) was added for a mixing time of 15 minutes (protected from light), followed by addition of 100 μl of 2 M $H_2SO_4$ for measurement. The absorbance was measured using an ELISA reader (Thermo Scientific 5250500 Microplate reader Varioscan Flash LemiSens option) with the built-in software Skanit RE for Varioskan Flash 2.4.3. With respect to the plate template, 96-well Greiner Bio-One, flat bottom plate was selected, and the wavelength of 450 nm was used to measure the absorbance.

8-3 Result

Figure 10:
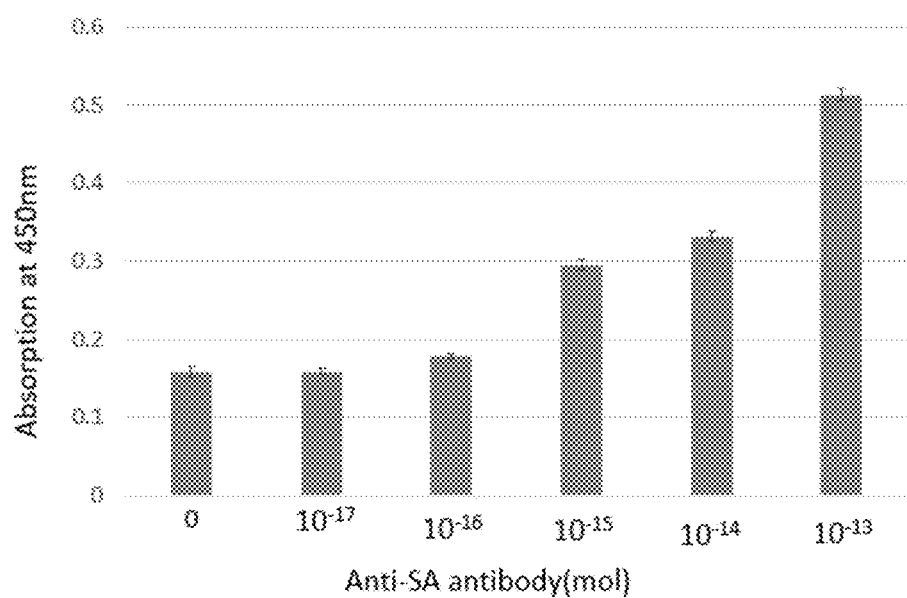
FIG. 10 shows the results of detection of anti-streptavidin antibody by ELISA using spores and HRP/3,3',5,5'-tetramethylbenzidine (TMB).

It was found that when the antibody amount was $10^{-16}$ mol, there was a difference between presence and absence of the antibody in terms of absorbance (see FIG. 10).

Example 9: Detection of β-Galactosidase by ELISA Using Spores and TMB

9-1 Preparation of ELISA Plate

The ELISA plate (GeneDireX/2115-196J) was washed 3 times with 200 μl of PBS/T (PBS with 0.05% Tween 20), followed by addition of 1 μl of anti-β-galactosidase antibody (Novusbio/NBP2-52702) at the concentration of 1 mg/ml and 100 μl of coating buffer (1.89 g $NaHCO_3$ and 0.954 g $Na_2CO_3$ in 500 mL $H_2O$). After being placed at 4° C. for 18 hours, the plate was washed 3 times with 200 μl of PBS/T, followed by addition of 200 μl of 5% skim milk. After 90 minutes, the plate was washed 3 times with 200 μl of PBS/T.

9-2 ELISA

1000 μl of spores (B.s. 168/pSH-SA) with $OD_{600}$ of 1 (about $5 \times 10^7$ spores/mL) was centrifuged under 12000×g for 3 minutes, followed by removing the supernatant and adding 80 μl of PBS, 10 μl of biotinylated anti-β-galactosidase antibody (abcam/ab6645) at the concentration of $10^{-8}$ M and 10 μl of an anti-spore antibody (mybiosource/mbs612878) at the concentration of $10^{-8}$ M and mixing for 2 hours. The mixture was then centrifuged under 12000×g for 3 minutes, followed by removing the supernatant and adding 100 μl of PBS (repeated twice). 1 μl of β-galactosidase at different concentrations was then added for mixing for 2 hours. The mixture was centrifuged under 12000×g for 3 minutes and the supernatant was removed; the precipitate was mixed with 100 μl of PBS (repeated twice). The solution was added to the ELISA plate as prepared above for a mixing step of 2 hours. Afterward, the plate was washed 3 times with 200 μl of PBS/T; to the plate was then added 100 μl of goat-anti-rabbit IgG (HRP) (abcam/ab6721) at the concentration of 0.2 μg/ml for a mixing time of 30 minutes, followed by washing 10 times with 200 μl of PBS/T (each time includes an immersing step of 2 minutes). 100 μl of TMB Substrate (Thermo Scientific/34021) was added for a mixing time of 15 minutes (protected from light), followed by addition of 100 μl of 2 M $H_2SO_4$ for measurement. The absorbance was measured using an ELISA reader (Thermo Scientific 5250500 Microplate reader Varioscan Flash LemiSens option) with the built-in software Skanit RE for Varioskan Flash 2.4.3. With respect to the plate template, 96-well Greiner Bio-One flat bottom plate was selected, and the wavelength of 450 nm was used to measure the absorbance.

9-3 Result

Figure 11:
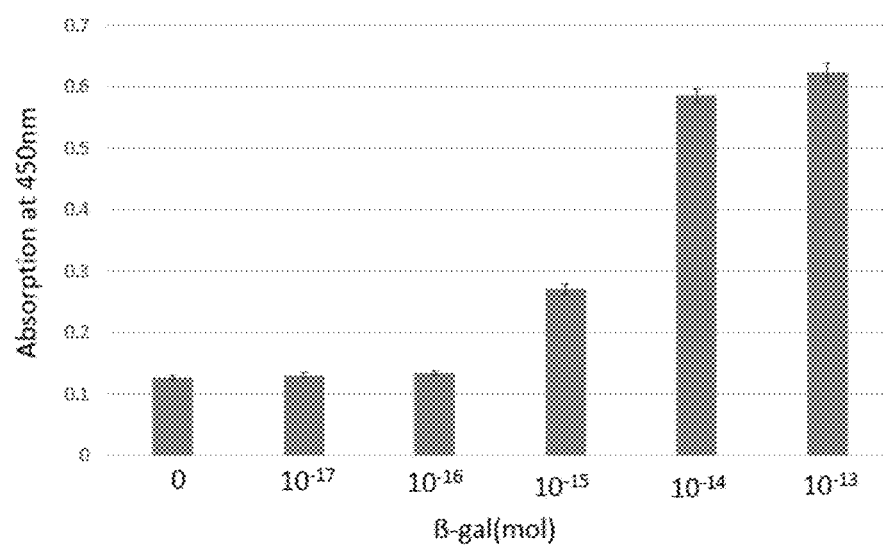
FIG. 11 shows the results of detection of β-galactosidase by ELISA using spores and TMB.

It was found that when the β-galactosidase amount was $10^{-15}$ mol, there was a significant difference between presence and absence of β-galactosidase in terms of absorbance, and the greater the β-galactosidase amount is, the greater the absorbance is (see FIG. 11).

Example 10: Detection of Anti-Streptavidin Antibody by ELISA Using E. Coli and TMB

10-1 Preparation of ELISA Plate

The ELISA plate (GeneDireX/2115-196J) was washed 3 times with 200 μl of PBS/T (PBS with 0.05% Tween 20), followed by addition of 1 μl of a goat-anti-mouse IgG antibody (SIGMA/M8890) at the concentration of 2 mg/ml and 100 μl of coating buffer (1.89 g $NaHCO_3$ and 0.954 g $Na_2CO_3$ in 500 mL $H_2O$). After being placed at 4° C. for 18 hours, the plate was washed 3 times with 200 μl of PBS/T, followed by addition of 200 μl of 5% skim milk. After 90 minutes of blocking, the plate was washed 4 times with 200 μl of PBS/T.

10-2 ELISA

200 μl of MG1655/pH-SA-eGFP with $OD_{600}$ of 10 was centrifuged under 12000×g for 3 minutes, followed by removing the supernatant and adding 90 μl of PBS and 10 μl of a mouse anti-streptavidin antibody (abcam/ab10020) at different concentrations for mixing for 2 hours under room temperature. The mixture was then centrifuged under 12000×g for 3 minutes, followed by removing the supernatant and adding 100 μl of PBS. The solution was added to the ELISA plate as prepared above for a mixing step of 2 hours. Afterward, the plate was washed 3 times with 200 μl of PBS/T; to the plate was then added 100 μl of a goat-anti-rabbit IgG (HRP) antibody (abcam/ab6721) at the concentration of 0.2 μg/ml for a mixing time of 30 minutes, followed by washing 10 times with 200 μl of PBS/T (each time includes an immersing step of 2 minutes). 100 μl of TMB Substrate (Thermo Scientific/34021) was added for a mixing time of 15 minutes (protected from light), followed by addition of 100 μl of 2 M $H_2SO_4$ (as stop solution) for measurement. The absorbance was measured using an ELISA reader (Thermo Scientific 5250500 Microplate reader Varioscan Flash LemiSens option) with the built-in software Skanit RE for Varioskan Flash 2.4.3. With respect to the plate template, 96-well Greiner Bio-One, flat bottom plate was selected, and the wavelength of 450 nm was used to measure the absorbance.

10-3 Result

Figure 12:
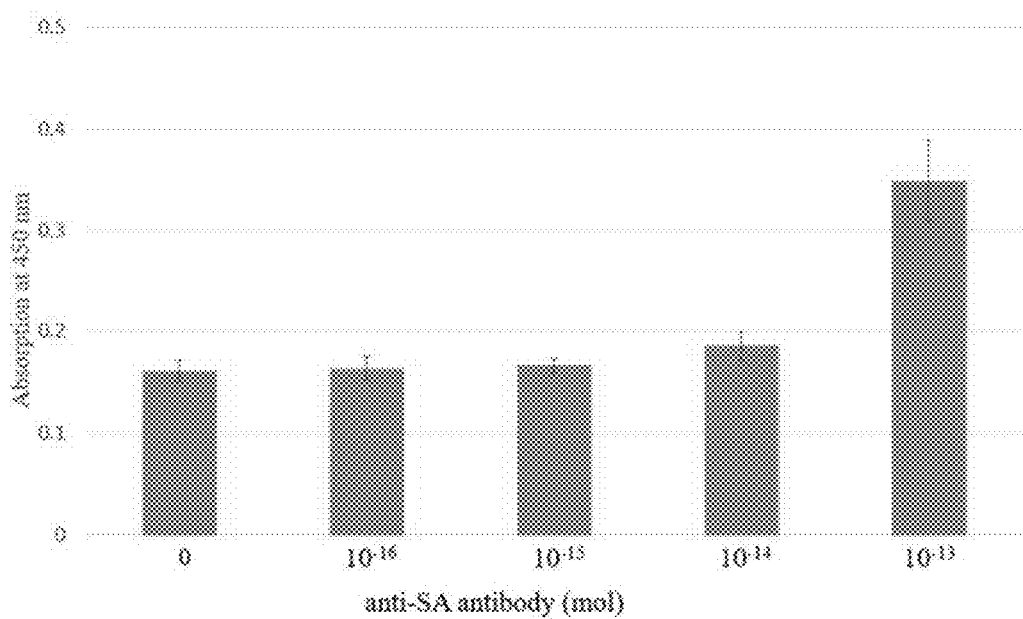
FIG. 12 shows the results of detection of anti-streptavidin antibody by ELISA using E. coli and TMB.

It was found that when the antibody amount was $10^{-14}$ mol, there was a difference between presence and absence of the antibody in terms of absorbance, and the greater the antibody amount is, the greater the absorbance is (see FIG. 12).

Example 11: Detection of Anti-Streptavidin Antibody by Flow Cytometry Using Spores

11-1 Pretreatment of Spores

To 1000 μl of spores (B.s. 168/pSH-SA) with $OD_{600}$ of 1 was added 250 μl of 0.05% SDS and mixed for 30 minutes. The mixture was centrifuged twice (under 12000×g for 3 minutes), followed by addition of 1000 μl 1% BSA (w/v, BSA/PBS) and a mixing step of 2 hours. The $OD_{600}$ of the spores was adjusted to 0.1.

11-2 Sample Mixture

10 μl of spores with $OD_{600}$ of 0.1 was mixed with 10 μl of an anti-streptavidin antibody (abcam/ab10020) (from mouse) at different concentrations for 2 hours, followed by centrifuging and washing twice and adding PBS so that the total volume was 100 μl. 3.33 μl of a goat anti-mouse IgG fluorescein isothiocyanate (FITC) secondary antibody (Leinco Technologies, Inc., catalog no. M113) at the concentration of $1 \times 10^{-7}$ M was added for a mixing time of 1.5 hours followed by centrifuging and washing once. Another 10 μl of spores with $OD_{600}$ of 0.1 was mixed with 10 μl of PBS solution for 2 hours, followed by centrifuging and washing twice and adding PBS so that the total volume was 100 μl. 3.33 μl of a goat anti-mouse IgG fluorescein isothiocyanate (FITC) secondary antibody (Leinco Technologies, Inc., catalog no. M113) at the concentration of $1 \times 10^{-7}$ M was added for a mixing time of 1.5 hours followed by centrifuging and washing once (without addition of antibody to be detected, as a negative control group). The solution was injected into a flow cytometer (CytoFLEX Flow Cytometer; Beckman Coulter; CO2946).

11-3 Data Manipulation

The charts of Fluorescence Activated Cell Sorting (FACS) were analyzed using the built-in CytExpert software. We define the fluorescent spore as the spore containing fluorescence intensity greater than the fluorescence intensity ($4 \times 10^3$ for this case) of the right bottom of the main peak of the waveform in the FACS chart for the negative control. Hence, the amount of the fluorescent spores is the sum of numbers of spores whose fluorescence intensity is greater than $4 \times 10^3$.

11-4 Result

Figure 13:
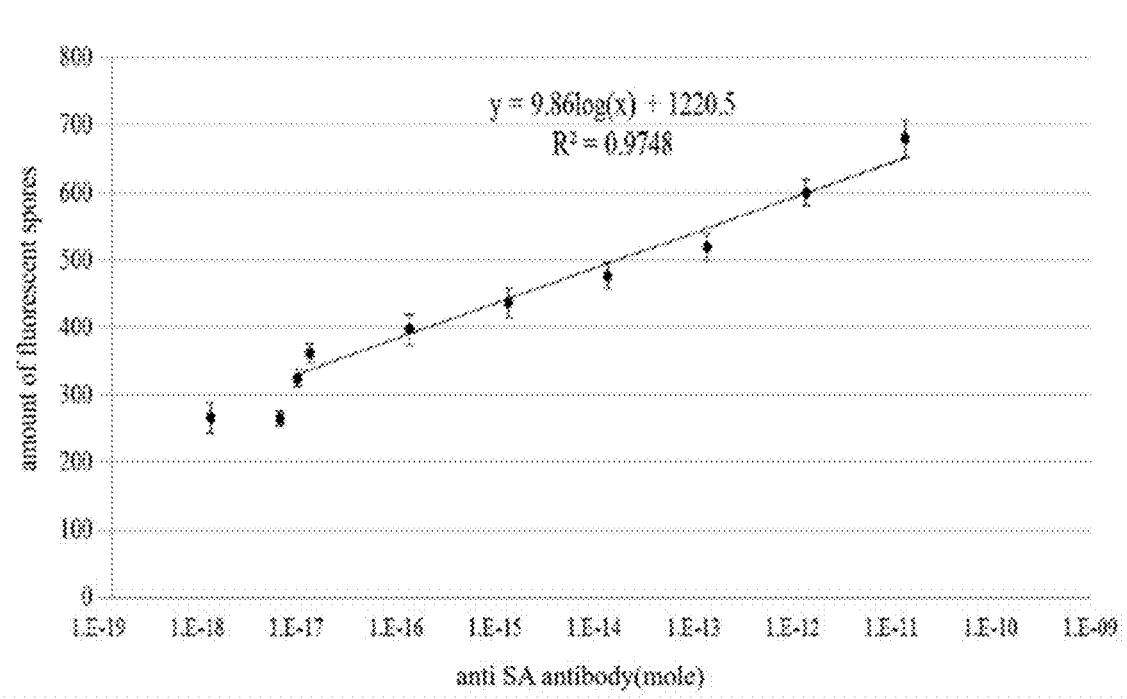
FIG. 13 shows the results of detection of anti-streptavidin antibody by flow cytometry using spores.

In FIG. 13, the x-axis is log scaled to represent the amount of the target antibody, and y-axis represents the data measured; the plotted graph is shown in FIG. 13. It was found that an antibody amount of $1 \times 10^{-17}$ mol could be detected, and the result is shown in FIG. 13. The slope of the target antibody between $10^{-11}$ mol and $10^{-17}$ mol is 9.86, $R^2$: 0.9748.

Example 12: Detection of β-Galactosidase by Flow Cytometry Using Spores 12-1 Pretreatment of Spores To 1000 μl of spores (B.s. 168/pSH-SA) with $OD_{600}$ of 1 was added 250 μl of 0.05% (w/v) SDS and mixed for 30 minutes. The mixture was centrifuged twice (under 12000×g for 3 minutes), followed by addition of 1000 μl 1% BSA (w/v, BSA/PBS) and a mixing step of 2 hours. The $OD_{600}$ of the spores was adjusted to 0.1. Afterward, 100 μl of the spores and 100 μl of a biotinylated anti-β-gal antibody (abcam/ab6645) at the concentration of $10^{-7}$ M were mixed overnight, followed by centrifuging and washing twice and adding 100 μl of PBS at pH 7.4 and the $OD_{600}$ of the spores was adjusted to 0.1.

12-2 Mixture of Fluorescence Group

100 μl of a goat anti-mouse IgG-FITC antibody (Leinco Technologies, Inc., catalog no. M113) at the concentration of $1 \times 10^{-7}$ M and 100 μl of an anti-β-gal antibody from mouse (Novusbio/NBP2-52702) at the concentration of $1 \times 10^{-7}$ M were mixed overnight.

12-3 Sample Mixture

10 μl of spores with $OD_{600}$ of 0.1 was mixed with 10 μl of β-galactosidase at different concentrations for 2 hours, followed by addition of PBS to bring the total volume to 100 μl, centrifuging and washing twice and adding 3.33 μl of the fluorescence group for a mixing time of 1.5 hour. Another 10 μl of spores with $OD_{600}$ of 0.1 was mixed with 3.33 μl of the fluorescence group for 60 minutes, followed by addition of PBS to bring the total volume to 100 μl (without addition of β-galactosidase to be detected, as the control group). The solution was injected into a flow cytometer (CytoFLEX Flow Cytometer; Beckman Coulter; CO2946).

12-4 Data Manipulation

The charts of Fluorescence Activated Cell Sorting (FACS) were analyzed using the built-in CytExpert software. We define the fluorescent spore as the spore containing fluorescence intensity greater than the fluorescence intensity ($3 \times 10^3$ for this case) of the right bottom of the main peak of the waveform in the FACS chart for the negative control. Hence, the amount of the fluorescent spores is the sum of numbers of spores whose fluorescence intensity is greater than $3 \times 0^3$.

12-5 Result

Figure 14:
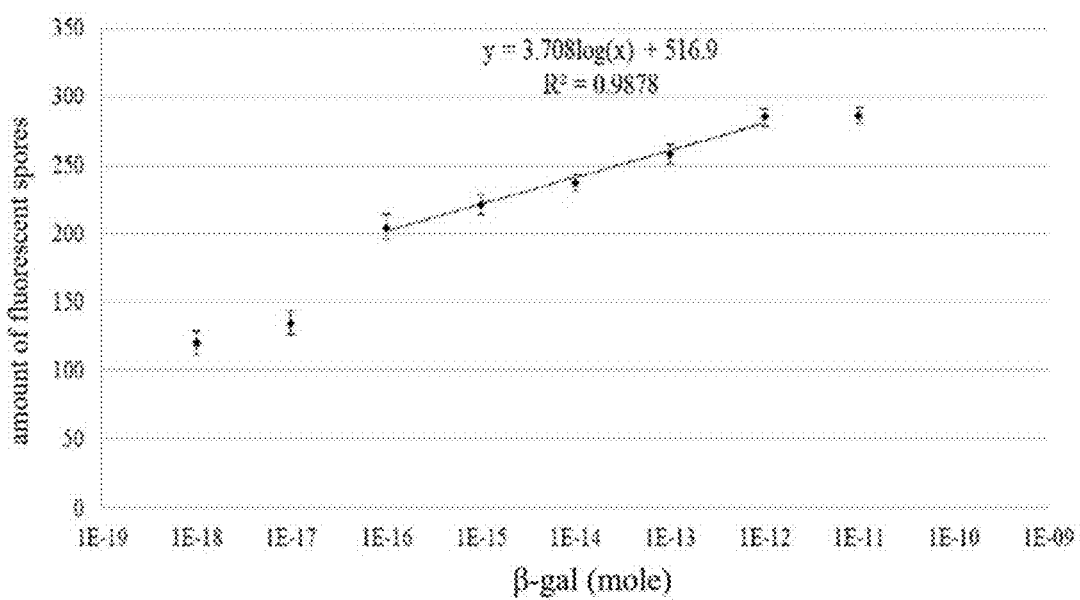
FIG. 14 shows the results of detection of β-galactosidase by flow cytometry using spores.

In FIG. 14, the x-axis is log scaled to represent the amount of β-galactosidase, and y-axis represents the data measured; the plotted graph is shown in FIG. 14. It was found that a β-galactosidase amount of $1 \times 10^{-16}$ mol could be detected, and the result is shown in FIG. 14. The slope of β-galactosidase between $10^{-12}$ mol and $10^{-16}$ mol is 3.708, $R^2$: 0.9878.

Example 13: Detection of Biotin by Flow Cytometry Using Spores 13-1 Pretreatment of Spores To 100 μl of spores (B.s. 168/pSH-SA) or 100 μl of spores (B.s. 168) with $OD_{600}$ of 1 was added 20 μl of 0.05% (w/v) SDS and 880 μl of PBS and mixed for 30 minutes. The mixture was centrifuged and washed twice (under 12000×g for 3 minutes), followed by addition of 1000 μl PBS and the $OD_{600}$ of the spores was adjusted to about 0.01.

13-2 Sample Mixture

200 μl of the pretreated B.s. 168/pSH-SA spores was mixed with 20 μl of biotin at different concentrations for 1 minute, followed by addition of 2 μl of $2 \times 10^{-5}$ M biotin-fluorescein (Biotium, 80019) and mixing for 5 minutes. Another 200 μl of the pretreated B.s. 168 spores with $OD_{600}$ of 0.01 was mixed with 2 μl of $2 \times 10^{-5}$ M biotin-fluorescein (Biotium, 80019) and mixing for 5 minutes (as the control group). The solution was injected into a flow cytometer (CytoFLEX Flow Cytometer; Beckman Coulter; C02946).

13-3 Data Manipulation

The charts of Fluorescence Activated Cell Sorting (FACS) were analyzed using the built-in CytExpert software. We define the fluorescent spore as the spore containing fluorescence intensity greater than the fluorescence intensity ($2 \times 10^3$ for this case) of the right bottom of the main peak of the waveform in the FACS chart for the control. Hence, the amount of the fluorescent spores is the sum of numbers of spores whose fluorescence intensity is greater than $2*10^3$.

13-4 Result

Figure 15:
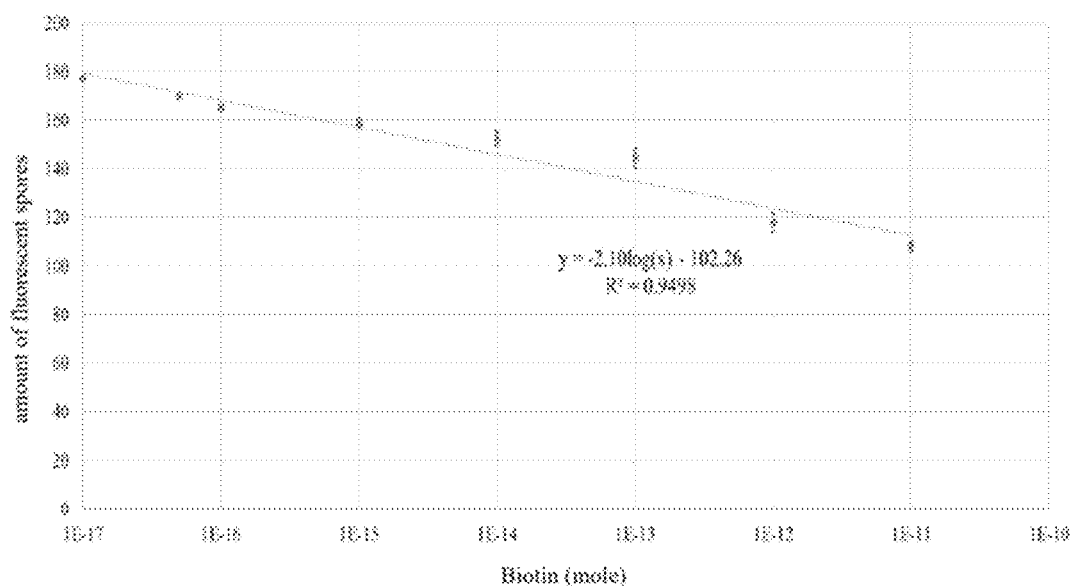
FIG. 15 shows the results of detection of biotin by flow cytometry using spores.

In FIG. 15, the x-axis is log scaled to represent the amount of biotin, and y-axis represents the data measured; the plotted graph is shown in FIG. 15. It was found that a biotin amount of $5 \times 10^{-17}$ mol could be detected, and the result is shown in FIG. 15. The slope of biotin between $10^{-11}$ mol and $10^{-17}$ mol is −2.10, $R^2$: 0.9498.

Example 14: Detection of β-Galactosidase by Conventional LFA Using Gold Nanoparticles (AuNP)

14-1 AuNP Modification

100 μl of potassium carbonate solution at the concentration of 26 mM was added to 600 μl of AuNP solution (0.355 nM) (final concentration: AuNP solution at 0.3 nM; potassium carbonate solution at 3.714 mM). 1 μl of biotinylated anti-β-gal antibody (abcam/ab6645) (from rabbit) at the concentration of 2 mg/ml was added and the mixture was placed at 4° C. for 16 hours, followed by addition of 200 μl of 5% BSA and waiting for 30 minutes. The mixture was then centrifuged under 4000×g at 4° C. for 40 minutes. Afterward, the supernatant was removed, and the precipitate was resuspended with 600 μl of PBS; the solution was stored at 4° C. for use.

14-2 Strip Preparation 1 mg/ml of anti-β-galactosidase antibody (Novusbio/NBP2-52702) and 2 mg/mL of goat anti-rabbit IgG antibody (abcam/ab6702) were respectively dispensed to the positive line and the negative line on the membrane (Millipore/HF1200) (2 μl per cm on the membrane), followed by a drying step at room temperature for 2 hours. The membrane was then immersed in 1% PVA for 30 minutes followed by a drying step at room temperature for 2 hours. Afterward, the membrane was immersed in 5% sucrose solution for 30 seconds. After being dried, the membrane was cut into strips with a width of 0.5 cm and stored at 4° C.

14-3 Detection

The modified AuNP was mixed thoroughly with 1 µl of β-galactosidase at different concentrations. Afterward, the strip was immediately placed in the above solution mixture, and a photograph was taken to record the result after drying for about 10 minutes.

14-4 Result

Figure 16:
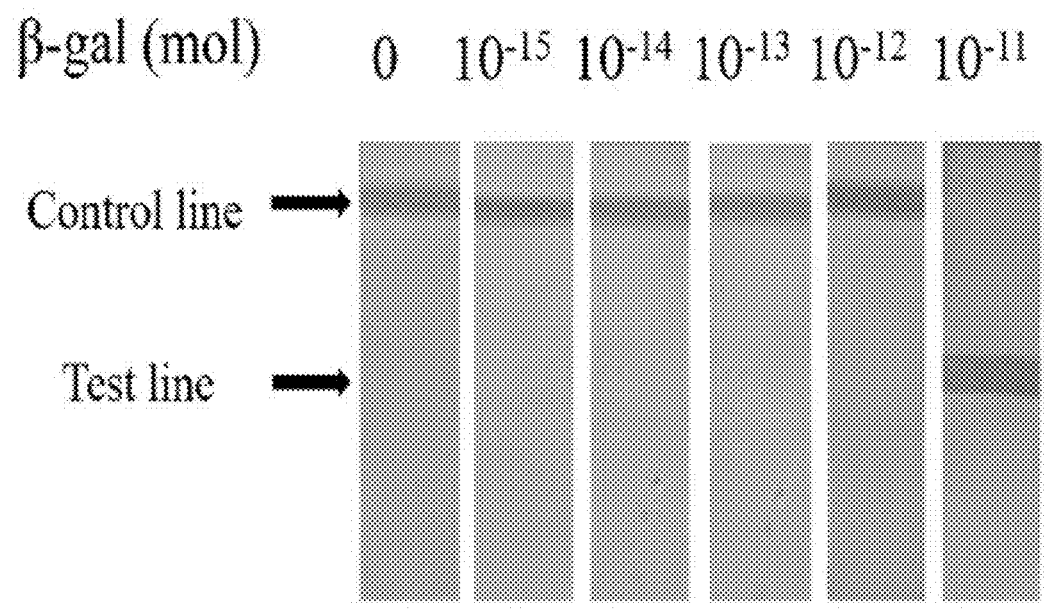
FIG. 16 shows the results of detection of β-galactosidase by conventional LFA using gold nanoparticles.

It was found that when the amount of β-galactosidase is $10^{-12}$ mol, the positive line shows a faint signal, and the higher the β-galactosidase concentration is, the stronger the signal is (see FIG. 16). Furthermore, there is no signal in the positive line for the samples containing β-galactosidase of $10^{-13}$ mol, $10^{-14}$ mol, or $10^{-15}$ mol.

Clearly, the sensitivity of the detection system of the present invention with respect to detection of β-galactosidase by LFA using spores and AuNP (as demonstrated in Example 3) is increased 1,000-fold compared with conventional LFA methods.

REFERENCES

Engvall, E. and Perlmann, P. (1972). "Enzyme-linked immunosorbent assay, Elisa." The Journal of Immunology. 109 (1): 129-135.

Lequin, R. M. (2005). "Enzyme Immunoassay (EIA)/Enzyme-Linked Immunosorbent Assay (ELISA)." Clinical Chemistry. 51 (12): 2415-8.

Schmidt, S D; Mazzella, M J; Nixon, R A; Mathews, P M (2012). Aβ measurement by enzyme-linked immunosorbent assay. Methods in Molecular Biology. 849. pp. 507-27.

Chittamma, A., S. J. Marin, J. A. Williams, C. Clark and G. A. McMillin Detection of In Utero Marijuana Exposure by GC-MS, Ultra-Sensitive ELISA and LC-TOF-MS Using Umbilical Cord Tissue. Journal of Analytical Toxicology 2013; 37: 391-394.

Kim, H. J., Jeong, H., Lee, S. J. "Synthetic biology for microbial heavy metal biosensors" (2018) Analytical and Bioanalytical Chemistry, 410, pp. 1191-1203

Sany, S. B. T., Narimani, L., Soltanian, F. K., Hashim, R., Rezayi, M., Karlend, D. J., Mahmud, H. N. M. E. "An overview of detection techniques for monitoring dioxin-like compounds: latest technique trends and their applications" (2016) RSC Adv. 6, pp. 55415-55429

Gui, Q., Lawson, T., Shan, S., Yan, L., Liu, Y. "The Application of Whole Cell-Based Biosensors for Use in Environmental Analysis and in Medical Diagnostics" (2017) Sensors, 17, 1623; doi:10.3390/s17071623

Bereza-Malcolm, L. T., Mann, G., Franks, A. E. "Environmental sensing of heavy metals through whole cell microbial biosensors: a synthetic biology approach" (2015) ACS Synth Biol., 4, pp. 535-46.

Mehta, J., Bhardwaj, S. K, Bhardwaj, N., Paul, A. K., Kumar, P., Kim, K. H. "Progress in the biosensing techniques for trace-level heavymetals." (2016) Biotechnol Adv., 34, pp. 47-60.

Liu, Q.; Wu, C.; Cai, H.; Hu, N.; Zhou, J.; Wang, P. Cell-based biosensors and their application in biomedicine. Chem. Rev. 2014, 114, 6423-6461.

Tian, Y; Lu, Y; Xu, X.; Wang, C.; Zhou, T.; Li, X. Construction and comparison of yeast whole-cell biosensors regulated by two RAD54 promoters capable of detecting genotoxic compounds. Toxicol. Mech. Methods 2017, 27, 115-120.

Xu, T., Young. A., Marr, E., Sayler, G., Ripp, S., Close, D. "A rapid and reagent-free bioassay for the detection of dioxin-like compounds and other aryl hydrocarbon receptor (AhR) agonists using autobioluminescent yeast" (2018) Analytical and Bioanalytical Chemistry 410, pp. 1247-1256.

Dusserre, C., Mollergues, J., Lo Piparo, E., Smieško, M., Marin-Kuan, M., Schilter, B., Fussell, K. "Using bisphenol A and its analogs to address the feasibility and usefulness of the CALUX-PPARγ assay to identify chemicals with obesogenic potential" (2018) Toxicology in Vitro, 53, pp. 208-221.

Steinberg, P., Behnisch, P. A., Besselink, H., Brouwer, A. A., "Screening of molecular cell targets for carcinogenic heterocyclic aromatic amines by using calux reporter gene assays" (2017) Cell Biology and Toxicology, 33, pp. 283-293.

Nguyen, Q A., Schumann, W. "Use of IPTG-inducible promoters for anchoring recombinant proteins on the *Bacillus subtilis* spore surface" (2014) Protein Expression and Purification, 95, pp. 67-76.

Francisco, J., CHARLES F. EARHART, AND GEORGE GEORGIOU. Transport and anchoring of β-lactamase to the external surface of *Escherichia coli*. Proc. Natl. Acad. Sci. USA, Vol. 89, pp. 2713-2717, April 1992, Biochemistry.

Georgiou, G., Daren L. Stephens, Christos Stathopoulos, Heather L. Poetschke, John Mendenhalls and Charles F. Earhart. Display of pMactamase on the *Escherichia coli* surface: outer membrane phenotypes conferred by Lpp'-OmpA'-β-lactamase fusions. Protein Engineering vol. 9 no. 2 pp. 239-247. 1996.

Sullivan, M. A., Yasbin, R. E., Young, F. E. "New shuttle vectors for *Bacillus subtilis* and *Escherichia coli* which allow rapid detection of inserted fragments." (1984) Gene, 29 (1-2), pp. 21-26.

Argarana, C. E., Kuntz, I. D., Birken, S., Axel, R. and Cantor, C. R. "Molecular cloning and nucleotide sequence of the streptavidin gene." (1986) Nucleic Acids Res, 14 (4), pp. 1871-1882.

Duc le H, Hong H A, Atkins H S, Flick-Smith H C, Durrani Z, Rijpkema S, Titball R W, Cutting S M: Immunization against anthrax using *Bacillus subtilis* spores expressing the anthrax protective antigen. Vaccine 2007; 25: 346-355.

Errington, J. Regulation of endospore formation in *Bacillus subtilis*. Nature Reviews *Microbiol* 2003, 1, pp. 117-126.

Henriques A O, Costa T, Martins L O, Zilhao R: Functional architecture and assembly of the spore coat; in Ricca E, Henriques A O, Cutting S M (eds): Bacterial Spore Formers: Probiotics and Emerging Applications. London, Horizon Science Press, 2004, pp. 34-52.

Hinc K, Iwanicki A, Obuchowski M: New stable anchor protein and peptide linker suitable for successful spore surface display in *B. subtilis*. Microb Cell Fact 2013; 12: 22.

Hinc K, Isticato R, Dembek M, Karczewska J, Iwanicki A, Peszynska-Sularz G, De Felice M, Obuchowski M, Ricca E: Expression and display of UreA of *Helicobacter acinonychis* on the surface of *Bacillus subtilis* spores. MicrobCell Fact 2010b; 9: 2.

Isticato R, Cangiano G, Tran H T, Ciabattini A, Medaglini D, Oggioni M R, et al. 2001. Surface display of recombinant proteins on *Bacillus subtilis* spores. J. Bacteriol. 183: 6294-6301.

Isticato R, Ricca E. 2014. Spore Surface Display. Microbiol. Spectr. 2(5).

Katarzyna M. Koczula and Andrea Gallotta. Lateral flow assays. *Essays in Biochemistry* (2016) 60: 111-120.

Kim J, Schumann W: Display of proteins on *Bacillus subtilis* endospores. Cell Mol Life Sci 2009; 66: 3127-3136.

Kunst F., Ogasawara N., Moszer I., Albertini A. M., Alloni G., Azevedo V., Bertero M. G., Bessières P. et al., The complete genome sequence of the gram-positive bacterium *Bacillus subtilis*. *Nature* 1997, 390 (6657), 249-256.

Kwon S J, Jung H C, Pan J G: Transgalactosylation in a water-solvent biphasic reaction system with beta-galactosidase displayed on the surfaces of *Bacillus subtilis* spores. Appl Environ Microbiol 2007; 73: 2251-2256.

McKenney, P T., Driks, A., Eichenberger, P. "The *Bacillus subtilis* endospore: assembly and functions of the multi-layered coat" (2013) Nature Reviews Microbiology, 11, pp. 33-44.

Mohab A. Al-Hinai, Shawn W. Jones, Eleftherios T. Papoutsakis. The Clostridium Sporulation Programs: Diversity and Preservation of Endospore Differentiation Mohab A. *Microbiology and Molecular Biology Reviews* 2015, 79 (1), pp. 19-37.

Pan J G, Kim E J, Yun C H: *Bacillus* spore display. Trends Biotechnol 2012; 30: 610-612. Rowley, T Flow Cytometry—A Survey and the Basics. *MATER METHODS* 2012, 2: 125.

Setlow, P. Germination of Spores of *Bacillus* Species: What We Know and Do Not Know. *Journal of Bacteriology* 2014, 196 (7), pp. 1297-1305.

Smith, G. P., Filamentous fusion phage: Novel expression vectors that display cloned antigens on the virion surface. *Science* 1985, 228 (4705), pp. 1315-1317.

Takamatsu H, Watabe K: Assembly and genetics of spore protective structures. Cell Mol Life Sci 2002; 59: 434-444.

Taylor, R. G.; Walker, D. C.; McInnes, R. R., *E. coli* host strains significantly affect the quality of small scale plasmid DNA preparations used for sequencing. *Nucleic Acids Research* 1993, 21 (7): 1677-1678.

Van Bloois E, Winter R T, Kolmar H, Fraaije M W: Decorating microbes: surface display of proteins on *Escherichia coli*. Trends Biotechnol 2011; 29: 79-86.

Yuan Y, Feng F, Chen L, Yao Q, Chen K: Surface display of *Acetobacter pasteurianus* AdhA on *Bacillus subtilis* spores to enhance ethanol tolerance for liquor industrial potential. Eur Food Res Technol 2013; 238: 285-293.

Zeigler, D. R.; Pragai, Z.; Rodriguez, S.; Chevreux, B.; Muffler, A.; Albert, T.; Bai, R.; Wyss, M.; Perkins, J. B., The origins of 168, W23, and other *Bacillus subtilis* legacy strains. *J Bacteriol* 2008, 190 (21): 6983-95.

Barat, Bhaswati; Wu, Anna M. (2007). "Metabolic biotinylation of recombinant antibody by biotin ligase retained in the endoplasmic reticulum." *Biomolecular Engineering*. 24 (3): 283-91. doi:10.1016/j.bioeng.2007.02.003. PMC 2682619

Negri A, Potocki W, Iwanicki A, Obuchowski M, Hinc K. (2013). "Expression and display of *Clostridium difficile* protein FliD on the surface of *Bacillus subtilis* spores." J Med Microbiol., 62: 1379-1385. 10.1099/jmm.0.057372-0.

Ning Z, Peng Y, Hao W, Duan C, Rock D L, Luo S. (2011). "Generation of recombinant Orf virus using an enhanced green fluorescent protein reporter gene as a selectable marker." BMC Vet Res., 7: 80-10.1186/1746-6148-7-80.

The invention claimed is:

1. A system for detecting the presence of an analyte in a sample, comprising (a) a recombinant *Escherichia coli* (*E. coli*) expressing one or more identical or different recombinant proteins on the surface thereof, wherein at least one of the recombinant proteins specifically binds to the analyte directly or through a binding agent that specifically binds to said recombinant protein and the analyte, and (b) a signal-producing substance that can be detected, and wherein the system is a diagnostic kit.

2. The system of claim 1, wherein the analyte is a compound, an antibody, or a protein molecule.

3. The system of claim 1, wherein each of the one or more identical or different recombinant proteins expressed on the surface of the recombinant *E. coli* comprises an exogenous protein independently selected from streptavidin, avidin, enhanced green fluorescent protein (eGFP), green fluorescent protein (GFP), red fluorescent protein (RFP), yellow fluorescent protein (YFP), catalase, laccase, beta-galactosidase, luciferase, beta-lactamase, a protein specifically or non-specifically binding to the analyte or binding agent, an antibody, an antigen, protein A, protein G, protein L, and protein A/G.

4. The system of claim 3, wherein the one or more recombinant proteins expressed on the surface of the recombinant *E. coli* comprise eGFP and/or streptavidin.

5. The system of claim 3, wherein the one or more recombinant proteins expressed on the surface of the recombinant *E. coli* are fusion proteins.

6. The system of claim 5, wherein the fusion proteins comprise a membrane protein of the recombinant *E. coli* and the exogenous protein.

7. The system of claim 6, wherein the exogenous protein is streptavidin, avidin, protein A, protein G, protein L, and/or protein A/G.

8. The system of claim 1, wherein the binding agent is an antibody against the analyte.

9. The system of claim 8, wherein the antibody is conjugated with biotin or other protein-binding molecules.

10. The system of claim 1, wherein the signal-producing substance comprises dye, fluorescent dye, fluorescent protein, colloidal gold nanoparticles, nanoparticles with color, or enzymes capable of converting a substrate providing no signal to a substrate providing a signal.

11. The system of claim 10, wherein the signal-producing substance is for detecting the binding of the at least one recombinant protein to the analyte or for detecting the binding of the binding agent to the analyte.

12. The system of claim 1, wherein the system further comprises a competing agent that competes for the binding of the analyte to the at least one recombinant protein or binding agent.

13. The system of claim 12, wherein the competing agent itself is a signal-producing substance.

14. The system of claim 11, wherein the detecting agent is an antibody or an antigen which specifically binds to the analyte.

15. The system of claim 1, wherein the system further comprises (a) a membrane with a positive region and a negative region, wherein antibodies, antigens or competing agents are immobilized in the positive region and/or the negative region for detecting presence or absence of analyte in the sample; or (b) an ELISA plate with proteins capable of binding to the analyte, antibodies, antigens, or competing agents immobilized therein, for detecting presence or absence of analyte in the sample.

16. The system of claim 15, wherein the membrane is a nitrocellulose membrane.

17. A method of detecting an analyte in a sample using the system of claim 1, wherein the binding of the at least one recombinant protein to the analyte is detected by flow cytometry, lateral flow, or ELISA.

* * * * *